(12) United States Patent
Chaoui

(10) Patent No.: US 12,133,688 B2
(45) Date of Patent: *Nov. 5, 2024

(54) METHODS, SYSTEMS AND DEVICES FOR PRE-OPERATIVELY PLANNED ADAPTIVE GLENOID IMPLANTS

(71) Applicant: Stryker European Operations Limited, Carrigtwohill (FR)

(72) Inventor: Jean Chaoui, Lyons (FR)

(73) Assignee: Stryker European Operations Limited, Carrigtwohill (IE)

(*) Notice: Subject to any disclaimer, the term of this patent is extended or adjusted under 35 U.S.C. 154(b) by 850 days.

This patent is subject to a terminal disclaimer.

(21) Appl. No.: 16/855,277

(22) Filed: Apr. 22, 2020

(65) Prior Publication Data

US 2020/0246077 A1   Aug. 6, 2020

Related U.S. Application Data

(60) Continuation of application No. 16/153,941, filed on Oct. 8, 2018, now Pat. No. 10,660,709, which is a
(Continued)

(51) Int. Cl.
*A61B 34/00* (2016.01)
*A61B 34/10* (2016.01)
(Continued)

(52) U.S. Cl.
CPC ............ *A61B 34/10* (2016.02); *A61B 90/361* (2016.02); *A61F 2/30942* (2013.01);
(Continued)

(58) Field of Classification Search
CPC .......... A61F 2/38; A61F 2/389; A61F 2/3868; A61F 2/30; A61F 2/30942; A61F 34/10; A61F 2/4081; A61B 34/10
See application file for complete search history.

(56) References Cited

U.S. PATENT DOCUMENTS 5,370,692 A   12/1994   Fink et al.
5,725,586 A    3/1998   Sommerich
(Continued)

FOREIGN PATENT DOCUMENTS

CA   3203261 A1   7/2022
EP   1323395 A2   7/2003
(Continued)

OTHER PUBLICATIONS

Intent to Grant from counterpart Canadian Application No. 2,938,709 dated Mar. 6, 2023, 1 pp.
(Continued)

*Primary Examiner* — Jason-Dennis N Stewart
(74) *Attorney, Agent, or Firm* — Shumaker & Sieffert, P.A.

(57) ABSTRACT

Methods, systems and devices for pre-operatively planned shoulder surgery guides and implants. Pre-operative planning methods for designing glenoid implants and prostheses, particularly with patient-specific augmentation, based on considerations of multiple factors affecting the outcome of shoulder surgery. Methods of using surgery guides and implants, including adaptive glenoid implants, in patients undergoing shoulder surgery.

31 Claims, 13 Drawing Sheets

Related U.S. Application Data division of application No. 15/034,398, filed as application No. PCT/IB2014/002593 on Nov. 10, 2014, now abandoned.

(60) Provisional application No. 61/901,750, filed on Nov. 8, 2013.

(51) Int. Cl.
  *A61B 90/00* (2016.01)
  *A61F 2/30* (2006.01)
  *A61F 2/40* (2006.01)
  *A61F 2/46* (2006.01)

(52) U.S. Cl.
  CPC ...... *A61F 2/4081* (2013.01); *A61B 2034/107* (2016.02); *A61F 2002/30736* (2013.01); *A61F 2002/30878* (2013.01); *A61F 2002/30884* (2013.01); *A61F 2002/30948* (2013.01); *A61F 2002/4632* (2013.01)

(56) References Cited

U.S. PATENT DOCUMENTS

| | | | |
|---|---|---|---|
| 6,459,948 B1 | 10/2002 | Ateshian et al. | |
| 6,699,289 B2 * | 3/2004 | Iannotti | A61B 17/1684 623/19.13 |
| 6,772,026 B2 | 8/2004 | Bradbury et al. | |
| 6,944,518 B2 | 9/2005 | Roose | |
| 7,468,075 B2 | 12/2008 | Lang et al. | |
| 7,542,791 B2 | 6/2009 | Mire et al. | |
| 7,618,451 B2 | 11/2009 | Berez et al. | |
| 7,747,305 B2 | 6/2010 | Dean et al. | |
| 7,799,077 B2 | 9/2010 | Lang et al. | |
| 7,837,621 B2 | 11/2010 | Krause et al. | |
| 7,981,158 B2 | 7/2011 | Fitz et al. | |
| 7,983,777 B2 | 7/2011 | Melton et al. | |
| 8,062,302 B2 | 11/2011 | Lang et al. | |
| 8,105,330 B2 | 1/2012 | Fitz et al. | |
| 8,160,325 B2 | 4/2012 | Zug et al. | |
| 8,160,345 B2 | 4/2012 | Pavlovskaia et al. | |
| 8,175,683 B2 | 5/2012 | Roose | |
| 8,214,016 B2 | 7/2012 | Lavallee et al. | |
| 8,221,430 B2 | 7/2012 | Park et al. | |
| 8,231,634 B2 | 7/2012 | Mahfouz et al. | |
| 8,337,501 B2 | 12/2012 | Fitz et al. | |
| 8,337,507 B2 | 12/2012 | Lang et al. | |
| 8,350,186 B2 | 1/2013 | Jones et al. | |
| 8,377,073 B2 | 2/2013 | Wasielewski | |
| 8,382,765 B2 | 2/2013 | Axelson et al. | |
| 8,444,651 B2 | 5/2013 | Kunz et al. | |
| 8,457,930 B2 | 6/2013 | Schroeder | |
| 8,480,753 B2 | 7/2013 | Collazo et al. | |
| 8,532,361 B2 | 9/2013 | Pavlovskaia et al. | |
| 8,532,806 B1 | 9/2013 | Masson | |
| 8,532,807 B2 | 9/2013 | Metzger | |
| 8,535,319 B2 | 9/2013 | Ball | |
| 8,545,509 B2 | 10/2013 | Park et al. | |
| 8,551,169 B2 | 10/2013 | Fitz et al. | |
| 8,585,708 B2 | 11/2013 | Fitz et al. | |
| 8,617,174 B2 | 12/2013 | Axelson, Jr. et al. | |
| 8,617,242 B2 | 12/2013 | Philipp | |
| 8,634,617 B2 | 1/2014 | Tsougarakis et al. | |
| 8,638,998 B2 | 1/2014 | Steines et al. | |
| 8,682,052 B2 | 3/2014 | Fitz et al. | |
| 8,709,089 B2 | 4/2014 | Lang et al. | |
| 8,734,455 B2 | 5/2014 | Park et al. | |
| 8,735,773 B2 | 5/2014 | Lang | |
| 8,764,836 B2 | 7/2014 | De Wilde et al. | |
| 8,775,133 B2 | 7/2014 | Schroeder | |
| 8,777,875 B2 | 7/2014 | Park | |
| 8,801,719 B2 | 8/2014 | Park et al. | |
| 8,808,302 B2 | 8/2014 | Roose et al. | |
| 8,830,233 B2 | 9/2014 | Friedland et al. | |
| 8,843,229 B2 | 9/2014 | Vanasse et al. | |
| 8,864,769 B2 | 10/2014 | Stone et al. | |
| 8,864,834 B2 | 10/2014 | Boileau et al. | |
| 8,884,618 B2 | 11/2014 | Mahfouz | |
| 8,898,043 B2 | 11/2014 | Ashby et al. | |
| 8,903,530 B2 | 12/2014 | Metzger | |
| 8,932,361 B2 | 1/2015 | Tornier et al. | |
| 8,934,961 B2 | 1/2015 | Lakin et al. | |
| 8,971,606 B2 | 3/2015 | Chaoui et al. | |
| 8,984,731 B2 | 3/2015 | Broeck et al. | |
| 8,986,309 B1 | 3/2015 | Murphy | |
| 8,989,460 B2 | 3/2015 | Mahfouz | |
| 8,990,052 B2 | 3/2015 | Lavallee et al. | |
| 8,992,538 B2 | 3/2015 | Keefer | |
| 9,011,456 B2 | 4/2015 | Ranawat et al. | |
| 9,020,788 B2 | 4/2015 | Lang et al. | |
| 9,060,788 B2 | 6/2015 | Bollinger | |
| 9,066,806 B2 | 6/2015 | Phipps | |
| 9,084,617 B2 | 7/2015 | Lang et al. | |
| 9,107,679 B2 | 8/2015 | Lang et al. | |
| 9,138,258 B2 | 9/2015 | Geebelen | |
| 9,180,015 B2 | 11/2015 | Fitz et al. | |
| 9,186,161 B2 | 11/2015 | Lang et al. | |
| 9,198,732 B2 | 12/2015 | Iannotti et al. | |
| 9,204,977 B2 | 12/2015 | Bollinger | |
| 9,220,516 B2 | 12/2015 | Lang et al. | |
| 9,232,955 B2 | 1/2016 | Bonin, Jr. et al. | |
| 9,237,950 B2 | 1/2016 | Hensley et al. | |
| 9,278,413 B2 | 3/2016 | Sperling | |
| 9,289,221 B2 | 3/2016 | Gelaude et al. | |
| 9,295,482 B2 | 3/2016 | Fitz et al. | |
| 9,301,812 B2 | 4/2016 | Kehres et al. | |
| 9,308,091 B2 | 4/2016 | Lang | |
| 9,320,608 B2 | 4/2016 | Sperling | |
| 9,326,780 B2 | 5/2016 | Wong et al. | |
| 9,345,548 B2 | 5/2016 | Schoenefeld et al. | |
| 9,351,743 B2 | 5/2016 | Kehres et al. | |
| 9,381,026 B2 | 7/2016 | Trouilloud et al. | |
| 9,386,994 B2 | 7/2016 | Agnihotri et al. | |
| 9,408,698 B2 | 8/2016 | Miles et al. | |
| 9,414,928 B2 | 8/2016 | Sperling | |
| 9,421,021 B2 | 8/2016 | Keppler | |
| 9,451,973 B2 | 9/2016 | Heilman et al. | |
| 9,498,233 B2 | 11/2016 | Bash | |
| 9,504,579 B2 | 11/2016 | Mahfouz et al. | |
| 9,554,910 B2 | 1/2017 | Vanasse et al. | |
| 9,575,931 B2 | 2/2017 | Ratron | |
| 9,579,106 B2 | 2/2017 | Lo et al. | |
| 9,579,110 B2 | 2/2017 | Bojarski et al. | |
| 9,592,128 B2 | 3/2017 | Phipps | |
| 9,597,201 B2 | 3/2017 | Bollinger | |
| 9,615,834 B2 | 4/2017 | Agnihotri et al. | |
| 9,615,840 B2 | 4/2017 | Iannotti et al. | |
| 9,649,170 B2 | 5/2017 | Park et al. | |
| 9,662,214 B2 | 5/2017 | Li et al. | |
| 9,668,873 B2 | 6/2017 | Winslow et al. | |
| 9,675,461 B2 | 6/2017 | Mahfouz | |
| 9,684,768 B2 | 6/2017 | Lavallee et al. | |
| 9,693,785 B2 | 7/2017 | Theiss et al. | |
| 9,713,533 B2 | 7/2017 | Taylor et al. | |
| 9,713,539 B2 | 7/2017 | Haimerl et al. | |
| 9,715,563 B1 | 7/2017 | Schroeder | |
| 9,717,508 B2 | 8/2017 | Iannotti et al. | |
| 9,737,367 B2 | 8/2017 | Steines et al. | |
| 9,741,263 B2 | 8/2017 | Iannotti et al. | |
| 9,757,238 B2 | 9/2017 | Metzger | |
| 9,763,682 B2 | 9/2017 | Bettenga | |
| 9,775,680 B2 | 10/2017 | Bojarski et al. | |
| 9,795,393 B2 | 10/2017 | Hughes et al. | |
| 9,808,261 B2 | 11/2017 | Gelaude et al. | |
| 9,814,533 B2 | 11/2017 | Park et al. | |
| 9,820,868 B2 | 11/2017 | Witt et al. | |
| 9,839,438 B2 | 12/2017 | Eash | |
| 9,895,230 B2 | 2/2018 | Mahfouz | |
| 9,913,691 B2 | 3/2018 | Brooks | |
| 9,925,048 B2 | 3/2018 | Winslow et al. | |
| 9,936,962 B2 | 4/2018 | Heilman et al. | |
| 9,937,046 B2 | 4/2018 | Mahfouz | |
| 9,987,024 B2 | 6/2018 | Frey et al. | |
| 9,993,341 B2 | 6/2018 | Vanasse et al. | |

(56) References Cited

U.S. PATENT DOCUMENTS

| | | |
|---|---|---|
| 10,010,334 B2 | 7/2018 | Keppler |
| 10,010,431 B2 | 7/2018 | Eraly et al. |
| 10,016,811 B2 | 7/2018 | Neal |
| 10,019,551 B2 | 7/2018 | Zellner et al. |
| 10,022,137 B2 | 7/2018 | Theiss et al. |
| 10,034,757 B2 | 7/2018 | Kovacs et al. |
| 10,052,114 B2 | 8/2018 | Keppler et al. |
| 10,052,206 B2 | 8/2018 | Mahfouz |
| 10,092,419 B2 | 10/2018 | Hananouchi et al. |
| 10,102,309 B2 | 10/2018 | McKinnon et al. |
| 10,130,378 B2 | 11/2018 | Bryan |
| 10,159,513 B2 | 12/2018 | Pavlovskaia et al. |
| 10,172,715 B2 | 1/2019 | De Wilde et al. |
| 10,195,036 B2 | 2/2019 | Ratron |
| 10,195,043 B2 | 2/2019 | Taylor et al. |
| 10,206,688 B2 | 2/2019 | Park et al. |
| 10,213,311 B2 | 2/2019 | Mahfouz |
| 10,251,755 B2 | 4/2019 | Boileau et al. |
| 10,262,084 B2 | 4/2019 | Lavallee et al. |
| 10,349,953 B2 | 7/2019 | Park et al. |
| 10,405,993 B2 | 9/2019 | Deransart et al. |
| 10,413,416 B2 | 9/2019 | Boileau et al. |
| 10,426,493 B2 | 10/2019 | Kehres et al. |
| 10,426,495 B2 | 10/2019 | Bonin, Jr. et al. |
| 10,426,549 B2 | 10/2019 | Kehres et al. |
| 10,441,298 B2 | 10/2019 | Eash |
| 10,463,497 B2 | 11/2019 | Sperling |
| 10,537,390 B2 | 1/2020 | Varadarajan et al. |
| 10,543,100 B2 | 1/2020 | Couture et al. |
| 10,548,668 B2 | 2/2020 | Furrer et al. |
| 10,575,958 B2 | 3/2020 | Cardon et al. |
| 10,600,515 B2 | 3/2020 | Otto et al. |
| 10,624,655 B2 | 4/2020 | Iannotti et al. |
| 10,624,755 B2 | 4/2020 | Amis et al. |
| 10,660,709 B2 | 5/2020 | Chaoui |
| 10,667,867 B2 | 6/2020 | Gangwar et al. |
| 10,675,063 B2 | 6/2020 | Pavlovskaia et al. |
| 10,722,310 B2 | 7/2020 | Luby |
| 10,736,697 B2 | 8/2020 | Chaoui et al. |
| 10,762,623 B2 | 9/2020 | Geebelen et al. |
| 10,842,510 B2 | 11/2020 | Heilman et al. |
| 10,842,512 B2 | 11/2020 | Bonin, Jr. et al. |
| 10,888,378 B2 | 1/2021 | Walch |
| 10,898,348 B2 | 1/2021 | Vivanz et al. |
| 10,905,562 B2 | 2/2021 | Sbaiz et al. |
| 10,912,571 B2 | 2/2021 | Pavlovskaia et al. |
| 10,922,448 B2 | 2/2021 | Mckinnon et al. |
| 10,925,658 B2 | 2/2021 | Hopkins |
| 10,973,535 B2 | 4/2021 | Iannotti et al. |
| 10,973,580 B2 | 4/2021 | Berend et al. |
| 11,020,183 B2 | 6/2021 | Gomes |
| 11,033,335 B2 | 6/2021 | Zhang |
| 11,039,889 B2 | 6/2021 | Frey et al. |
| 11,051,830 B2 | 7/2021 | Jaramaz et al. |
| 11,071,592 B2 | 7/2021 | McGuan et al. |
| 11,083,525 B2 | 8/2021 | Varadarajan et al. |
| 11,090,161 B2 | 8/2021 | Hodorek |
| 11,129,678 B2 | 9/2021 | Park |
| 11,134,963 B2 | 10/2021 | Buza et al. |
| 11,141,276 B2 | 10/2021 | Kehres |
| 11,166,733 B2 | 11/2021 | Neichel et al. |
| 11,166,764 B2 | 11/2021 | Roh et al. |
| 11,179,249 B2 | 11/2021 | Deransart et al. |
| 11,185,417 B2 | 11/2021 | Boileau et al. |
| 11,202,675 B2 | 12/2021 | Uhde et al. |
| 11,213,305 B2 | 1/2022 | Iannotti et al. |
| 11,234,721 B2 | 2/2022 | Gargac et al. |
| 11,253,323 B2 | 2/2022 | Hughes et al. |
| 11,278,299 B2 | 3/2022 | Neichel et al. |
| 11,278,413 B1 | 3/2022 | Lang |
| 11,298,118 B1 | 4/2022 | Koo |
| 11,298,140 B2 | 4/2022 | Wilkinson et al. |
| 11,298,142 B2 | 4/2022 | Park et al. |
| 11,298,188 B2 | 4/2022 | Kehres et al. |
| 11,298,189 B2 | 4/2022 | Kelman et al. |
| 11,337,762 B2 | 5/2022 | Mckinnon et al. |
| 11,344,370 B2 | 5/2022 | Park et al. |
| 11,399,851 B2 | 8/2022 | Neichel et al. |
| 11,399,894 B2 | 8/2022 | Chaoui et al. |
| 11,419,618 B2 | 8/2022 | Kehres et al. |
| 11,419,680 B2 | 8/2022 | Knotaxis et al. |
| 11,432,931 B2 | 9/2022 | Lang |
| 11,432,934 B2 | 9/2022 | Couture et al. |
| 11,471,303 B2 | 10/2022 | O'Grady |
| 11,488,721 B2 | 11/2022 | Otto et al. |
| 11,490,965 B2 | 11/2022 | Bischoff et al. |
| 11,490,966 B2 | 11/2022 | Roche et al. |
| 11,559,403 B2 | 1/2023 | Kehres |
| 11,596,479 B2 | 3/2023 | McGuan et al. |
| 11,602,360 B2 | 3/2023 | Heilman et al. |
| 11,617,591 B2 | 4/2023 | Eash |
| 11,621,086 B2 | 4/2023 | Spanberg et al. |
| 11,622,818 B2 | 4/2023 | Siemionow et al. |
| 11,653,976 B2 | 5/2023 | Bonny et al. |
| 11,660,197 B1 | 5/2023 | Lang |
| 11,696,833 B2 | 7/2023 | Casey |
| 11,712,302 B2 | 8/2023 | Walch |
| 11,717,412 B2 | 8/2023 | Casey et al. |
| 11,730,497 B2 | 8/2023 | Iannotti et al. |
| 11,737,883 B2 | 8/2023 | Metcalfe et al. |
| 11,751,946 B2 | 9/2023 | Gangwar et al. |
| 11,752,000 B2 | 9/2023 | Terill |
| 11,766,268 B2 | 9/2023 | Iannotti et al. |
| 11,766,336 B2 | 9/2023 | Penninger et al. |
| 11,819,415 B2 | 11/2023 | Metcalfe et al. |
| 11,847,755 B2 | 12/2023 | Park et al. |
| 11,850,158 B2 | 12/2023 | Simoes et al. |
| 11,883,040 B2 | 1/2024 | Bonin, Jr. et al. |
| 2001/0047210 A1 | 11/2001 | Wolf |
| 2002/0082741 A1 | 6/2002 | Mazumder et al. |
| 2004/0039259 A1 | 2/2004 | Krause et al. |
| 2004/0138754 A1 | 7/2004 | Lang et al. |
| 2004/0236424 A1 | 11/2004 | Berez et al. |
| 2004/0243148 A1 | 12/2004 | Bradbury et al. |
| 2005/0065617 A1 | 3/2005 | Moctezuma de la Barrera et al. |
| 2005/0065628 A1 | 3/2005 | Roose |
| 2005/0087047 A1 | 4/2005 | Farrar |
| 2005/0216305 A1 | 9/2005 | Funderud |
| 2006/0079963 A1 | 4/2006 | Hansen |
| 2006/0095047 A1 | 5/2006 | de la Barrera et al. |
| 2006/0136058 A1 | 6/2006 | Pietrzak |
| 2007/0118055 A1 | 5/2007 | McCombs |
| 2007/0118243 A1 | 5/2007 | Schroeder et al. |
| 2007/0203605 A1 | 8/2007 | Melton et al. |
| 2007/0233141 A1 | 10/2007 | Park et al. |
| 2008/0269596 A1 | 10/2008 | Revie et al. |
| 2008/0269906 A1 | 10/2008 | Iannotti et al. |
| 2008/0281328 A1 | 11/2008 | Lang et al. |
| 2008/0281329 A1 | 11/2008 | Fitz et al. |
| 2008/0281426 A1 | 11/2008 | Fitz et al. |
| 2008/0287954 A1 | 11/2008 | Kunz et al. |
| 2009/0216285 A1 | 8/2009 | Ek et al. |
| 2009/0276045 A1 | 11/2009 | Lang et al. |
| 2009/0318929 A1 | 12/2009 | Tornier et al. |
| 2010/0023015 A1 | 1/2010 | Park |
| 2010/0082035 A1 | 4/2010 | Keefer |
| 2010/0160917 A1 | 6/2010 | Fitz et al. |
| 2010/0222781 A1 | 9/2010 | Collazo et al. |
| 2010/0292963 A1 | 11/2010 | Schroeder |
| 2010/0303313 A1 | 12/2010 | Lang et al. |
| 2010/0305573 A1 | 12/2010 | Fitz et al. |
| 2010/0305574 A1 | 12/2010 | Fitz et al. |
| 2011/0029088 A1 | 2/2011 | Rausher et al. |
| 2011/0054478 A1 | 3/2011 | Vanasse et al. |
| 2011/0166661 A1 | 7/2011 | Boileau et al. |
| 2011/0190775 A1 | 8/2011 | Ure |
| 2011/0295329 A1 | 12/2011 | Fitz et al. |
| 2011/0304332 A1 | 12/2011 | Mahfouz |
| 2012/0041446 A1 | 2/2012 | Wong et al. |
| 2012/0041564 A1* | 2/2012 | Landon ............... A61F 2/30767 623/20.34 |
| 2012/0101503 A1 | 4/2012 | Lang et al. |
| 2012/0116203 A1 | 5/2012 | Vancraen et al. |
| 2012/0143267 A1 | 6/2012 | Iannotti et al. |

(56) References Cited

U.S. PATENT DOCUMENTS

| | | |
|---|---|---|
| 2012/0245647 A1 | 9/2012 | Kunz et al. |
| 2012/0276509 A1 | 11/2012 | Iannotti et al. |
| 2012/0289965 A1 | 11/2012 | Gelaude et al. |
| 2012/0303035 A1 | 11/2012 | Geebelen |
| 2013/0018378 A1 | 1/2013 | Hananouchi et al. |
| 2013/0024580 A1 | 1/2013 | Tsai et al. |
| 2013/0053968 A1 | 2/2013 | Nardini et al. |
| 2013/0110470 A1 | 5/2013 | Vanasse et al. |
| 2013/0110471 A1 | 5/2013 | Lang et al. |
| 2013/0211531 A1 | 8/2013 | Steines et al. |
| 2013/0338673 A1 | 12/2013 | Keppler |
| 2014/0142578 A1 | 5/2014 | Hananouchi et al. |
| 2014/0303938 A1 | 10/2014 | Schoenfeld et al. |
| 2014/0303990 A1 | 10/2014 | Schoenefeld et al. |
| 2014/0371863 A1 | 12/2014 | Vanasse et al. |
| 2015/0052586 A1 | 2/2015 | Mills et al. |
| 2015/0093283 A1 | 4/2015 | Miller et al. |
| 2015/0112348 A1 | 4/2015 | Schoenefeld et al. |
| 2015/0150688 A1 | 6/2015 | Vanasse et al. |
| 2015/0223941 A1 | 8/2015 | Lang |
| 2015/0342739 A1 | 12/2015 | Mahfouz |
| 2016/0067049 A1 | 3/2016 | Flaherty et al. |
| 2016/0074052 A1 | 3/2016 | Keppler et al. |
| 2016/0100907 A1 | 4/2016 | Gomes |
| 2016/0120555 A1 | 5/2016 | Bonin, Jr. et al. |
| 2016/0143749 A1 | 5/2016 | Holovacs et al. |
| 2016/0157937 A1 | 6/2016 | Kehres et al. |
| 2016/0166392 A1 | 6/2016 | Vanasse et al. |
| 2016/0184104 A1 | 6/2016 | Sperling |
| 2016/0192951 A1 | 7/2016 | Gelaude et al. |
| 2016/0193501 A1 | 7/2016 | Nipper et al. |
| 2016/0270854 A1 | 9/2016 | Chaoui |
| 2016/0296290 A1 | 10/2016 | Furrer et al. |
| 2016/0331467 A1 | 11/2016 | Slamin et al. |
| 2017/0000569 A1 | 1/2017 | Mahfouz |
| 2017/0000614 A1 | 1/2017 | Mahfouz |
| 2017/0035513 A1 | 2/2017 | Mahfouz et al. |
| 2017/0079803 A1 | 3/2017 | Lang |
| 2017/0105841 A1 | 4/2017 | Vanasse et al. |
| 2017/0119531 A1 | 5/2017 | Bojarski et al. |
| 2017/0143499 A1 | 5/2017 | Phipps |
| 2017/0150978 A1 | 6/2017 | Iannotti et al. |
| 2017/0151058 A1 | 6/2017 | Sperling |
| 2017/0273795 A1 | 9/2017 | Neichel et al. |
| 2017/0273801 A1 | 9/2017 | Hodorek |
| 2017/0281357 A1 | 10/2017 | Taylor et al. |
| 2017/0367766 A1 | 12/2017 | Mahfouz |
| 2018/0014835 A1 | 1/2018 | Lo et al. |
| 2018/0161176 A1 | 6/2018 | Vivanz et al. |
| 2018/0233222 A1 | 8/2018 | Daley et al. |
| 2018/0235642 A1 | 8/2018 | Amis et al. |
| 2018/0325526 A1 | 11/2018 | Haddad |
| 2019/0000629 A1 | 1/2019 | Winslow |
| 2019/0015118 A1 | 1/2019 | Neichel et al. |
| 2019/0015221 A1 | 1/2019 | Neichel et al. |
| 2019/0021866 A1 | 1/2019 | Vanasse et al. |
| 2019/0029757 A1 | 1/2019 | Roh et al. |
| 2019/0069913 A1 | 3/2019 | Iannotti et al. |
| 2019/0090952 A1 | 3/2019 | Bonny et al. |
| 2019/0142519 A1 | 5/2019 | Siemionow et al. |
| 2019/0201005 A1 | 7/2019 | Schoenefeld et al. |
| 2019/0269415 A1 | 9/2019 | Lo et al. |
| 2019/0365473 A1 | 12/2019 | Kehres et al. |
| 2020/0030034 A1 | 1/2020 | Kontaxis et al. |
| 2020/0078180 A1 | 3/2020 | Casey |
| 2020/0113632 A1 | 4/2020 | Varadarajan et al. |
| 2020/0155323 A1 | 5/2020 | Lang et al. |
| 2020/0170802 A1 | 6/2020 | Casey |
| 2020/0188121 A1 | 6/2020 | Boux de Casson et al. |
| 2020/0188134 A1 | 6/2020 | Mullen et al. |
| 2020/0253740 A1 | 8/2020 | Puncreobutr et al. |
| 2020/0281728 A1 | 9/2020 | Kulper et al. |
| 2020/0330161 A1 | 10/2020 | Chaoui et al. |
| 2020/0405330 A1 | 12/2020 | Bonin, Jr. et al. |
| 2021/0030477 A1 | 2/2021 | Zuhars et al. |
| 2021/0045888 A1 | 2/2021 | Sbaiz et al. |
| 2021/0068844 A1 | 3/2021 | Lo et al. |
| 2021/0085475 A1 | 3/2021 | Hodorek et al. |
| 2021/0128179 A1 | 5/2021 | Dupuis et al. |
| 2021/0128244 A1 | 5/2021 | Couture et al. |
| 2021/0196290 A1 | 7/2021 | Iannotti et al. |
| 2021/0228277 A1 | 7/2021 | Chaoui et al. |
| 2021/0259844 A1 | 8/2021 | Penninger et al. |
| 2021/0307833 A1 | 10/2021 | Farley et al. |
| 2021/0307911 A1 | 10/2021 | Metcalfe et al. |
| 2021/0315642 A1 | 10/2021 | McGuan et al. |
| 2021/0322130 A1 | 10/2021 | Penney et al. |
| 2021/0330389 A1 | 10/2021 | Varadarajan et al. |
| 2021/0338435 A1 | 11/2021 | Hodorek |
| 2021/0386435 A1 | 12/2021 | Buza et al. |
| 2022/0022895 A1 | 1/2022 | Neichel et al. |
| 2022/0031475 A1 | 2/2022 | Deransart et al. |
| 2022/0047278 A1 | 2/2022 | Fitz et al. |
| 2022/0054197 A1 | 2/2022 | Plessers et al. |
| 2022/0096240 A1 | 3/2022 | Neichel et al. |
| 2022/0110644 A1 | 4/2022 | Gargac et al. |
| 2022/0110685 A1 | 4/2022 | McGuan et al. |
| 2022/0125515 A1 | 4/2022 | McGuan et al. |
| 2022/0148454 A1 | 5/2022 | Jaramaz et al. |
| 2022/0160376 A1 | 5/2022 | Neichel et al. |
| 2022/0160405 A1 | 5/2022 | Casey et al. |
| 2022/0160439 A1 | 5/2022 | Ryan et al. |
| 2022/0183757 A1 | 6/2022 | Caldera et al. |
| 2022/0202497 A1 | 6/2022 | Janna et al. |
| 2022/0211507 A1 | 7/2022 | Simoes et al. |
| 2022/0249168 A1 | 8/2022 | Besier et al. |
| 2022/0257321 A1 | 8/2022 | Kehres et al. |
| 2022/0273450 A1 | 9/2022 | Steines et al. |
| 2022/0296259 A1 | 9/2022 | Shab |
| 2022/0313440 A1 | 10/2022 | Metcalfe et al. |
| 2022/0330957 A1 | 10/2022 | Neichel et al. |
| 2022/0338933 A1 | 10/2022 | Metcalfe et al. |
| 2022/0338998 A1 | 10/2022 | Sperling |
| 2022/0346968 A1 | 11/2022 | Pettersson et al. |
| 2022/0351828 A1 | 11/2022 | Chaoui |
| 2022/0370142 A1 | 11/2022 | Schoenefeld et al. |
| 2022/0387110 A1 | 12/2022 | Chaoui |
| 2022/0395376 A1 | 12/2022 | Poon et al. |
| 2023/0000645 A1 | 1/2023 | O'Grady |
| 2023/0045575 A1 | 2/2023 | Lang et al. |
| 2023/0048940 A1 | 2/2023 | Kontaxis et al. |
| 2023/0061695 A1 | 3/2023 | Couture et al. |
| 2023/0079807 A1 | 3/2023 | Metcalfe et al. |
| 2023/0085093 A1 | 3/2023 | Chaoui et al. |
| 2023/0085387 A1 | 3/2023 | Jones et al. |
| 2023/0109478 A1 | 4/2023 | Chaoui et al. |
| 2023/0148085 A1 | 5/2023 | Paul et al. |
| 2023/0181257 A1 | 6/2023 | McGuan et al. |
| 2023/0248435 A1 | 8/2023 | Bonny et al. |
| 2023/0317298 A1 | 10/2023 | Spanberg et al. |
| 2023/0329791 A1 | 10/2023 | Chaoui et al. |
| 2023/0346397 A1 | 11/2023 | Iannotti et al. |
| 2023/0346480 A1 | 11/2023 | Walch |
| 2023/0355401 A1 | 11/2023 | Metcalfe et al. |
| 2023/0363915 A1 | 11/2023 | Metcalfe et al. |
| 2023/0372018 A1 | 11/2023 | Gangwar et al. |
| 2023/0372111 A1 | 11/2023 | Terrill |

FOREIGN PATENT DOCUMENTS

| | | |
|---|---|---|
| EP | 2324801 A1 | 5/2011 |
| EP | 2471483 A1 | 7/2012 |
| EP | 1858430 B1 | 10/2013 |
| EP | 2670314 B1 | 8/2014 |
| EP | 2244654 B1 | 3/2017 |
| EP | 2770920 | 7/2017 |
| EP | 2770919 B1 | 8/2017 |
| EP | 3248553 | 11/2017 |
| EP | 2303192 B1 | 11/2018 |
| EP | 3760142 | 1/2021 |
| EP | 3845154 | 7/2021 |
| EP | 3481318 | 9/2022 |
| WO | 2005016123 | 2/2005 |
| WO | 2008021494 | 2/2008 |

(56) References Cited

FOREIGN PATENT DOCUMENTS

| WO | 2011110374 | | 9/2011 |
|---|---|---|---|
| WO | 2012141790 | A1 | 10/2012 |
| WO | 2012170376 | | 12/2012 |
| WO | 2013060851 | | 5/2013 |
| WO | 2013062848 | | 5/2013 |
| WO | 2013062851 | | 5/2013 |
| WO | 2013142998 | | 10/2013 |
| WO | 2014145267 | | 9/2014 |
| WO | 2014180972 | A2 | 11/2014 |
| WO | 2015018921 | | 2/2015 |
| WO | 2015052586 | A2 | 4/2015 |
| WO | 2015185219 | A1 | 12/2015 |
| WO | 2017091657 | A1 | 6/2017 |
| WO | 2017106294 | A2 | 6/2017 |
| WO | 2017184792 | A1 | 10/2017 |
| WO | 2017214537 | A1 | 12/2017 |
| WO | 2020104107 | A1 | 5/2020 |
| WO | 2020231656 | A2 | 11/2020 |
| WO | 2021026029 | | 2/2021 |
| WO | 2022147591 | | 7/2022 |
| WO | 2022169678 | | 8/2022 |
| WO | 2023200562 | | 10/2023 |

OTHER PUBLICATIONS

Response to Examination Report No. 1 dated Oct. 7, 2022, from counterpart Australian Application No. 2021205111, filed Feb. 27, 2023, 95 pp.
First Examination Report from counterpart Australian Application No. 2021205111 dated Oct. 7, 2022, p. 6.
Response to Office Action dated Apr. 4, 2022, from counterpart Canadian Application No. 2,938,709 filed Aug. 3, 2022, 17 pp.
Examination Report No. 1 from counterpart Australian Application No. 2021205111 dated Oct. 7, 2022, 6 pp.
Office Action from counterpart Canadian Application No. 2,938,709 dated Apr. 4, 2022, 3 pp.
Extended Search Report from counterpart European Application No. 21186701.5 dated Oct. 25, 2021, 8 pp.
Response to Office Action dated Aug. 12, 2021, from counterpart Canadian Application No. 2,938,709, filed Dec. 8, 2021, 10 pp.
Prosecution History from Australian Patent Application No. 2014347790, dated May 16, 2016 through Oct. 24, 2019, 388 pp. Downloaded in 5 parts.
Response to Examination Report No. 1 from counterpart Australian Application No. 2019236644, dated May 25, 2020, filed Jan. 15, 2021, 1 pp.
Examination Report No. 2 from counterpart Australian Application No. 2019236644, dated Jan. 25, 2021, 3 pp.
Response to Examination Report No. 2 from counterpart Australian Application No. 2019236644, dated Jan. 25, 2021, filed Apr. 16, 2021, 109 pp.
Notice of Acceptance from counterpart Australian Application No. 2019236644, dated Apr. 30, 2021, 3 pp.
Notice of Grant from counterpart Australian Application No. 2019236644, dated Aug. 26, 2021, 1 pp.
Office Action from counterpart Canadian Application No. 2,938,709, dated Aug. 12, 2021, 3 pp.
Response to Communication pursuant to Rules 161(1) and 162 EPC from counterpart European Application No. 14816382.7, dated Aug. 12, 2016, filed Feb. 17, 2017, 17 pp.
Communication pursuant to Article 94(3) EPC from from counterpart European Application No. 14816382.7, dated Jun. 18, 2018, 3 pp.
Response to Communication pursuant to Article 94(3) EPC from from counterpart European Application No. 14816382.7, dated Jun. 18, 2018, filed Dec. 10, 2018, 16 pp.
Communication under Rule 71(3) EPC from counterpart European Application No. 14816382.7, dated May 8, 2019, 129 pp.
Decision to Grant from counterpart European Application No. 14816382.7, dated Aug. 29, 2019, 2 pp.
Communication enclosing the extended European Search Report from counterpart European Application No. 19198726.2, dated Feb. 3, 2020, 5 pp.
Communication under Rule 71(3) EPC from counterpart European Application No. 19198726.2, dated Feb. 10, 2021, 125 pp.
Response to Communication under Rule 71(3) EPC from counterpart European Application No. 19198726.2, dated Feb. 10, 2021, filed Apr. 28, 2021, 4 pp.
Communication under Rule 71(3) EPC from counterpart European Application No. 19198726.2, dated May 26, 2021, 125 pp.
Decision to Grant from counterpart European Application No. 19198726.2, dated Aug. 19, 2021, 2 pp.
International Preliminary Report on Patentability from International Application No. PCT/IB2014/002593, dated May 10, 2016, 9 pp.
Prosecution History from U.S. Appl. No. 15/034,398, dated Aug. 9, 2017 through Jul. 6, 2018, 46 pp.
Prosecution History from U.S. Appl. No. 16/153,941, dated Feb. 10, 2020, 8 pp.
Boissonnat, J.D., "Shape Reconstruction from Planar Cross Sections," Computer Vision, Graphics, and Image Processing, vol. 44, No. 1, Oct. 1988, 29 pp.
Marker et al., "Contour-Based Surface Reconstruction using Implicit Curve Fitting, and Distance Field Filtering and Interpolation," Volume Graphics, Jan. 2006, 9 pp.
Nguyen et al., "A new segmentation method for MRI images of the shoulder joint," Fourth Canadian Conference on Computer and Robot Vision (CRV'07), May 2007, 8 pp.
Response to Office Action dated Mar. 28, 2023, from counterpart Australian Application No. 2021205111 filed Jul. 17, 2023, p. 100 pg.
Examination Report No. 2 from counterpart Australian Application No. 2021205111 dated Mar. 28, 2023, 4 pp.
First Examination Report issued in connection with corresponding Australian Patent Application No. 2019236644, dated May 25, 2020, 5 pages.
International Search Report and Written Opinion of the International Search Authority issued for corresponding PCT Patent Application No. PCT/IB2014/0024593 dated Feb. 26, 2015.
First Examination Report issued for corresponding Australian Patent Application No. 2014347790 dated Nov. 8, 2019, 5 pages.
Notice of Intent to Grant from counterpart Australian Application No. 2021205111 dated Aug. 21, 2023, 3 pp.
Response to Office Action dated Mar. 28, 2023, from counterpart Australian Application No. 2021205111 filed Jul. 17, 2023, 100 pp.
Office Action from U.S. Appl. No. 18/440,820 dated Apr. 25, 2024, 5 pp.
Favre, et al., "Influence of component positioning on impingement in conventional total shoulder arthroplasty" Clinical Biomechanics, Butterworth Scientifics, Nov. 5, 2007, pp. 175-183, vol. 23, No. 2, Guilford, GB.
Gregory, et al., "Accuracy of Glenoid Component Placement in Total Shoulder Arthroplasty and Its Effect on Clinical and Radiological Outcome in a Retrospective, Longitudinal, Monocentric Open Study," PLOS One, page e75791, Aug. 1, 2013, vol. 8, No. 10.
Jannotti et al., "Prosthetic positioning in total shoulder arthroplasty," Journal of Shoulder and Elbow Surgery, pp. S111-S121, Jan. 1, 2005, vol. 14, No. 1.
Nguyen et al., "Design and Development of a Computer Assisted Glenoid Implantation Technique for Shoulder Replacement Surgery," Computer Aided Surgery, vol. 12, No. 3, May 2007, pp. 152-159.
Raaijmakers et al., "A Custom-Made Guide-Wire Positioning Device for Hip Surface Replacement Arthroplasty: Description and First Results," BMC Musculoskeletal Disorders, vol. 11, Jul. 2010, 7 pp.
U.S. Appl. No. 18/440,820, filed Feb. 13, 2024, by Chaoui.

* cited by examiner

METHODS, SYSTEMS AND DEVICES FOR PRE-OPERATIVELY PLANNED ADAPTIVE GLENOID IMPLANTS

CROSS-REFERENCE TO RELATED APPLICATIONS

This application is a Continuation of U.S. patent application Ser. No. 16/153,941, filed Oct. 8, 2018, which is a divisional of U.S. patent application Ser. No. 15/034,398, filed May 4, 2016 (abandoned), which is a national phase entry under 35 U.S.C. 371 of International Patent Application PCT/IB2014/002593, filed Nov. 10, 2014, which claims the benefit of U.S. Provisional Patent Application No. 61/901,750, filed Nov. 8, 2013, which are incorporated herein by reference.

TECHNICAL FIELD

The presently disclosed subject matter relates to methods, systems and devices for pre-operatively planned adaptive glenoid implants and prostheses. The presently disclosed subject matter also relates to the use of such implants and prostheses in patients undergoing shoulder surgery.

BACKGROUND

Shoulder replacement is a common surgical operation that has achieved positive results for many patients. Indeed, approximately 10% of joint replacement procedures globally are related to the shoulder. Many shoulder procedures are performed in a patient where substantially normally bone exists for orientation and fixation of a prosthetic replacement, or resurfacing. In these cases, the need for the shoulder replacement can often times be related mostly to the arthritic condition of the joint, and relative absence of healthy cartilage.

In some patients, however, one or more of the bones of the shoulder are not only arthritic, but have also had previous conditions that have caused bone to wear away. In such cases, there may not be sufficient bone to adequately affix a prosthetic implant to the bone, or the bones may have been worn such that the orientation of a joint replacement cannot be satisfactorily determined to ensure a positive patient outcome.

There are a number of factors that complicate the selection, orientation and affixation of prosthetic implant devices, such as glenoid implants and/or humeral implants. Failure to properly account for each factor can lead to improperly sized, misaligned and/or poorly affixed implants that result in a poor surgical outcome for the patient.

In order to increase the likelihood of successful patient outcomes in patients undergoing shoulder surgery, methods, systems and devices are needed that allow for the full understanding and incorporation of all necessary factors for optimization of shoulder implant selection and placement. Thus, a need remains for methods, systems and devices for pre-operatively planned shoulder surgery guides and implants, such as glenoid implants and prostheses, that achieve desired outcomes.

SUMMARY

The presently disclosed subject matter provides methods, systems and devices for pre-operatively planned glenoid implants and prosthetic devices. The presently disclosed subject matter also provides methods of using glenoid implants in patients undergoing shoulder surgery.

An object of the presently disclosed subject matter having been stated hereinabove, and which is achieved in whole or in part by the presently disclosed subject matter, other objects will become evident as the description proceeds when taken in connection with the accompanying Examples as best described hereinbelow.

BRIEF DESCRIPTION OF THE DRAWINGS

The presently disclosed subject matter can be better understood by referring to the following figures. The components in the figures are not necessarily to scale, emphasis instead being placed upon illustrating the principles of the presently disclosed subject matter (often schematically). In the figures, like reference numerals designate corresponding parts throughout the different views. A further understanding of the presently disclosed subject matter can be obtained by reference to an embodiment set forth in the illustrations of the accompanying drawings. Although the illustrated embodiment is merely exemplary of systems for carrying out the presently disclosed subject matter, both the organization and method of operation of the presently disclosed subject matter, in general, together with further objectives and advantages thereof, may be more easily understood by reference to the drawings and the following description. The drawings are not intended to limit the scope of this presently disclosed subject matter, which is set forth with particularity in the claims as appended or as subsequently amended, but merely to clarify and exemplify the presently disclosed subject matter.

For a more complete understanding of the presently disclosed subject matter, reference is now made to the following drawings in which:

FIG. 18A depicts a glenoid implant with no back-side augmentation and FIG. 18B depicting a glenoid implant with back-side augmentation.

DETAILED DESCRIPTION

Figure 1A:
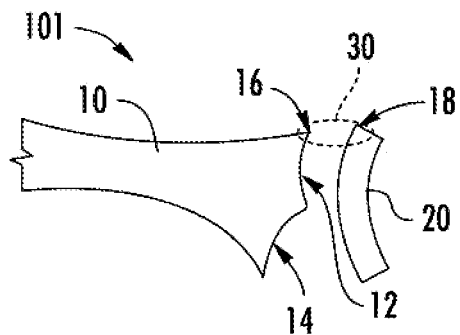
FIG. 1A is a schematic illustration of a step in a pre-operative planning method for designing a shoulder surgery guide where the anterior edge of a glenoid implant is aligned with an anterior edge of a glenoid bone, according to an embodiment of the disclosed subject matter.

Patients requiring shoulder surgery may have one or more of the bones of the shoulder that are not only arthritic, but may also have had previous conditions that have caused bone to wear away. In such cases, there may not be sufficient bone to adequately affix a prosthetic implant to the bone during a routine shoulder surgery. Indeed, the bones may have been worn such that the orientation of a joint replacement cannot be satisfactorily determined to ensure a positive patient outcome.

The glenoid bone can be subject to increased wear due to bone arthritic conditions of the joint, and due to alterations of a normal soft tissue envelope surrounding the joint. In such cases, the orientation of the face of the glenoid portion of the scapula bone may be altered so that the humeral bone is no longer appropriately apposed to the glenoid surface. In the case where the glenoid is severely worn, there can be two or more risks a surgeon must balance in an attempt to improve shoulder function and pain relief.

First, if the optimal orientation of the diseased but treated shoulder is not found and replicated with the prosthesis the patient may experience most operative complications related to subluxation or dislocation of the replaced shoulder joint. This can occur either due to passive inputs to the shoulder (e.g., leaning against it, or lying in bed), or due to active firing of surrounding soft tissue which is not able to be constrained by the replaced joint surfaces.

Additionally, the fixation of a replacement prosthesis, or implant, to the native patient bone can be problematic. Frequently, in order to counteract the risks associated with joint subluxation and dislocation described above, it can be necessary for a surgeon to orient or position the replacement prosthesis or implant in a position better suited to resist imbalanced muscle forces. In such cases, separation forces between the implant and the bone can increase, which in turn can increase the potential for loosening of the joint prosthesis in the bone. Implant loosening can be related to accelerated implant wear, bone erosion, increased tissue inflammation, joint synovitis, and pain.

In patients that have undergone shoulder replacement surgery, range of motion and strength are dependent on shoulder kinematics, which are in turn dependent on a host of factors. Such factor can, for example, include for example implant size, implant position, the design of implant shape, the joint line and soft tissue tension. In some cases it can be difficult to predict optimal implant size and position/orientation using currently available guides and implants. Often times a surgeon finds that there are too many variables to manage at one time. Moreover, the size choices of implants can be limited to the lowest practically functional groups to reduce economic burden to the health care system. Current implant designs and methodologies are inadequate to address these challenges because they are of significant cost, require time to develop, include increased risk of implant failure, and rely on human judgment of potential outcomes post-operatively.

There are many factors that can affect the optimal positioning of shoulder implants during replacement surgery. For example, such factors can include the patient size, relative bone wear, soft tissue strength and condition, six degrees-of-freedom positioning of the glenoid and/or the humeral prosthesis, selected implant size, preoperative patient activity and strength levels, post operative treatment protocols, size and density of patient bone. Additional factors can include patient smoking status, concomitant handicaps and/or patient problems. It can be quite difficult for a surgeon to understand and balance these factors simultaneously. In addition, only a few of these factors are able to be controlled by the surgeon. Finally, each factor does not necessarily have an equally weighted impact on patient outcome. Nevertheless, it is considered that the implant size, position, orientation and bone preparation of the glenoid and the humerus can have a significant impact on the surgical outcomes.

A factor that further complicates, or makes more difficult, a surgeons task of optimally placing a replacement component or implant to counteract these risk is the fact that the condition of the scapula is such that few landmarks exists for the surgeon the comprehend the implant position within the bone. Thus, frequently a surgeon might find that the implant position is not replicating as was envisioned during the surgical intervention.

Others have attempted to improve a surgeon's chance of providing successful patient outcomes by providing operative techniques and tools. What is missing, however, is the ability to fully understand and incorporate multiple factors to optimize the implant selection and placement. Specifically, in some embodiments, the success of the surgery can be highly dependent on both the selection of the matching prosthesis or prostheses (humeral and/or glenoid), as well as positioning of this prosthesis, as well as the soft tissue status before the surgery. There have been no previous attempts at including these factors in surgical planning and implant design.

Disclosed herein are methods, systems and devices for pre-operatively planned shoulder surgery guides, including glenoid placement guides, and implants. Methods, systems and devices are provided for the replacement of the shoulder joint, such as the glenohumeral joint, wherein the conditions of the humeral and soft tissue envelop is taken into consideration. More specifically, what is considered is that the shape and position of the glenoid implant is not based solely on what can be seen and measured on the scapula, but can be chosen, designed, planned and placed with incorporation of the same information related to the humerus. After all, the shoulder is a two part joint, i.e. glenoid and humeral head, wherein both parts work in conjunction with one another, and the factors that affect performance of the device can in some embodiments include factors from both sides of the joint.

Appropriate sizing of the prosthesis can be important to successful outcomes, knowing that oversized or "over-stuffed" replacement shoulders are more likely to dislocate, loosen, be painful, and/or have decreased range of motion. Replaced joints where the orientation of the prostheses is improper increases the likelihood of implant dislocation and loosening. Additionally, over-reaming, or too much bone removal, either on the glenoid, or the humerus, can be the cause of implant loosening, "under-stuffing" or inappropriate articular surface placement which can increase pain and decrease range of motion.

Provided herein in some embodiments is a glenoid implant designed and manufactured to specifically match the patient anatomy, including optimal humeral and/or glenoid implant size and shape, and taking into account one or more of the following factors: assessment of the humeral implant fit to the humeral bone; relative hardness of the patient bone preoperatively; height and diameter of the humeral head placed on the humeral stem; orientation, or "offset" of the humeral head; and optimal bone removal for preservation of soft tissue insertion and attachment.

In some embodiments, an adaptive glenoid implant as disclosed herein can comprise an augmented glenoid implant wherein the augmentation is included on the back side of the glenoid implant. A glenoid implant can comprise a central body, in some embodiments comprising a polyethylene material, wherein the central body comprises a lateral articulating surface on a first side (top side), sidewalls, a substantially flat second side (bottom side), and one or more pegs or keels extending from the second side. In some embodiments the central body, including the lateral articulating surface, can be substantially circular, oval or pear-shaped. In some embodiments, the shape of the glenoid implant approximates the shape of the natural glenoid cavity. In some aspects, the lateral articulating surface provides a surface upon which the humeral head can articulate.

In some embodiments, the augmentation of a glenoid disclosed herein can comprise an augmented feature or features extending from the second, or back side, of the glenoid implant. The second side of the glenoid implant is that which comes into contact with the bone of the scapula where the glenoid implant is seated, i.e. where the natural glenoid cavity was prior to insertion of the implant. Thus, the augmentation can in some embodiments enhance or improve the stability and contact between the glenoid implant and existing bone. In some aspects, an augmentation on the back side of a glenoid implant can be designed to align or match the shape and dimension of the cavity in the scapula where the glenoid is to be seated. By way of example and not limitation, in some aspects, the depth of the augmentation, size of the augmentation, and/or radial position of the augmentation on the second surface of the glenoid implant can be varied as desired given a particular situation, i.e. customized to fit the reamed glenoid cavity of the patient.

In some embodiments, a variable augmented glenoid implant or prosthesis is provided, wherein the variable augmentation is defined by one or more of the following: the depth of augmentation, the size of augmentation, the shape of the augmentation and/or the radial position of augmentation. By way of example and not limitation, the depth of the augmentation can range from about 2 mm to about 4 mm. Further, the augmentation can be small in size with respect to the size of the glenoid implant, e.g., can cover about 5%, 10%, 15%, 20%, 30%, 40%, 50%, or more of the back side of the glenoid implant, or can be large in size with respect to the size of the glenoid implant, e.g., can cover about 50%, 60%, 70%, 80%, 90%, 95% or greater of the back side of the glenoid implant. The shape of the augmentation can for example comprise a plate-like shape, sphere-like shape (fixed curvature, ellipsoid-like structure), cone like shape, a pyramid like shape or the like. The positioning of the augmentation on the second surface or back side of the glenoid can also vary, and can be located on the posterior and/or anterior side of the second surface, and/or at a superior and/or inferior location of the second surface of the glenoid implant. In some embodiments, the augmentation can be patient specific and/or patient tailored. In some aspects, the patient "specific" augmentation is generated by a geometric representation that best fits the joint surface, and does not consider that the joint surface necessarily needs to be altered in any way prior to implantation of the implant. In the case of a patient "tailored", the best fit implant is chosen, with a consideration for minimization of bone surface alteration to achieve minimally acceptable or optimal interface characteristics between the surface of the scapula bone and the implant. In some embodiments, the geometric representation can be plate (best fit plane), and/or spherical (best-fit-sphere), and/or ellipsoid (best-fit-ellipsoid). The radius of curvature could vary from ∞ to 10.

The geometric representation can depend on the wear surface and orientation. For example, a joint surface can be represented by 4 spheres with 4 different radi of curvature and 4 different sphere centers.

The augmentation can co-exist on the second surface of the glenoid implant along with a fixation component, e.g. a keel or peg. The fixation component can be located at any desirable position on the second surface of the glenoid implant, including for example in the center or medial position, at an inferior position, at a superior position, and/or in multiple locations, e.g. double fixation components.

In some aspects, the fixation component can have a free position on the backside surface and can be located according to the bony stock orientation of the patient in order to provide stable fixation and steady stress and strain distribution. The dimensions of the fixation elements can in some embodiments be patient tailored and their dimensions can be defined using correspondence matrix between a three dimensional (3D) bony structure of the patient and a statistical shape based atlas according to the following steps:
1. registration between patient bone and statistical shape model of the bone of interest;
2. extract the principle modes representing the patient bone;
3. define the fixation configuration (position and dimensions) according to the corresponding modes; and
4. apply collision detection to confirm the configuration of the bone fixation.

In some embodiments, the above method of creating an augmented glenoid implant or prosthesis based on pre-operative planning can further comprise one or more optimization steps. Such optimization steps can comprise identifying procedural risks by measuring to determine one or more of the following:
whether the glenoid face coverage is maximized;
whether the overhang of the glenoid face is minimized;
whether the bone removal on the glenoid face is minimized, such as for example less than about 2 mm of depth;
whether the glenoid retroversion is less than about 5 degrees;
whether the "seating" of the glenoid implant is greater than about 80%, i.e. about 80% of the back side of the glenoid implant is supported by or touching bone;
whether the depth of any glenoid implant augment feature is as minimal as possible;
whether there is less than about 1 mm of difference between the anatomic joint line and the new joint line with implants;
whether there is minimized penetration of the glenoid cortical wall medially;
whether there is maximized bone thickness behind the glenoid, preferably greater than 3 mm;
whether the orientation offset between the native glenoid and implant superior/inferior axis is minimized, preferably less than 5 degrees;
whether the superior or inferior tilt versus anatomy is minimized, preferably less than 5 degrees;
whether there is less than about 5% change in soft tissue length at extreme ranges of motion;
whether there is maximized filing of the humeral shaft, in some embodiments greater than 90% of intramedullary bone filled based on and identification of intramedullary bone by use of Houndsfield units;
whether there is an absence of a humeral head overhang compared to the cut, or prepared surface of the humeral bone;
whether there is minimal difference in diameter between anatomic and implant, in some embodiments less than 3 mm;
whether there is minimal difference in height between anatomic and implant, in some embodiments less than 1 mm; and
whether there is greater tuberosity to medial head edge comparison to anatomic, in some embodiments less than 2 mm.

The above methods can further comprise a step of recommending implants and placement positions, with recommended adjustments in glenoid implant size, augmentation depth, augment position, positioning in six degrees of freedom, fixation type, fixation size, reaming depth, reaming diameter, and reaming angle(s), seating ratio, wherein the reaming angles can comprise retroversion and inclination. The above method can further comprise a step of recommending implants and placement positions based on the reaming quantity, such as for example the quantity of removed cortical bone based on the Hounsfield units extracted directly from CT images. The above method can further comprise a step of recommending implants and placement positions, with recommended adjustments in humerus stem size, length, head diameter, head height, head offset and rotation (axial).

In some embodiments, the above methods can comprise pre-operative planning and designing of one or more variable augmented glenoid implants. The pre-operative planning methods and steps can optimize a glenoid implant with a custom designed augmentation(s) specific to a patient upon which the pre-operative planning was completed. By utilizing the disclosed pre-operative methods a variable augmented glenoid implant can be designed and constructed that increases the stability and contact between the glenoid implant and existing bone in the glenoid cavity. In some aspects, an augmentation on the back side of a glenoid implant can be designed and optimized to align or match the shape and dimension of the cavity in the scapula where the glenoid is to be seated. By way of example and not limitation, in some aspects, the depth of the augmentation, size of the augmentation, and/or radial position of the augmentation on the second surface of the glenoid implant can be varied as desired given a particular situation and/or a particular patient and based on pre-operative planning methods as disclosed herein.

In some embodiments, a method of creating a shoulder surgery guide comprises utilizing one or more of the above steps, analyses, optimizations and recommendations to create a shoulder surgery guide. Guide creation can comprise automated design and creation of a three dimensional model of a glenoid and/or humeral guide reflecting one or more optimized parameters determined during pre-operative planning based on the above method steps.

The subject matter described herein may be implemented in software in combination with hardware and/or firmware. For example, the subject matter described herein may be implemented in software executed by a processor. In one exemplary implementation, the subject matter described herein may be implemented using a computer readable medium having stored thereon computer executable instructions that when executed by the processor of a computer control the computer to perform steps. Exemplary computer readable media suitable for implementing the subject matter described herein include non-transitory devices, such as disk memory devices, chip memory devices, programmable logic devices, and application specific integrated circuits. In addition, a computer readable medium that implements the subject matter described herein may be located on a single device or computing platform or may be distributed across multiple devices or computing platforms.

Also provided herein are methods, systems and devices for creation of a glenoid implant or glenoid prosthesis based on pre-operative planning which takes into consideration a plurality of factors and assessments. In some embodiments, the creation of a glenoid implant based on pre-operative planning can comprise one or more of the following steps, the combination and order of which can vary: aligning an anterior edge of a glenoid implant with an anterior edge of a glenoid bone; adjusting a retroversion of the glenoid implant; adjusting an augmentation of the glenoid implant; adjusting an inferior tilt of the glenoid implant; evaluating bone support for the glenoid implant, wherein an amount of a rear surface of the glenoid implant that is supported by or touching bone is assessed; adjusting the medialization of the glenoid implant by assessing the volumetric amount of bone needed to be removed by reaming, or the minimum total distance of reaming necessary, in order to optimize the bone to implant interface; analyzing the fixation support in the absence of central pegs that penetrate a vault medially; analyzing the joint line, comprising comparing an original joint line and a new joint line, wherein the new joint line is substantially similar to the original joint line; measuring and matching widths of the glenoid implant and the glenoid bone after reaming and aligning inferior/superior axes of the glenoid implant and bone; assessing and adjusting as needed a thickness/height of the glenoid implant; assessing and adjusting as needed a depth of a glenoid fossa; assessing and adjusting as needed a thickness of a graft; determining a diameter of a humeral head; determining a height of the humeral head; determining a size of humeral bone implant from Houndsfield units measured by an imaging technique (e.g. computed tomography (CT) scan); and/or determining a best fit size of implant from a range of sizes, wherein the range of sizes is selected from the group consisting of length of stem, size of humeral stem, diameter of stem, size diameter of head, height of head, and offset of the center spherical head compared to the center of the face of the humeral stem.

In some embodiments, a pre-operative planning method for designing a glenoid implant is provided. Such a method can be separate from a pre-operative planning method for the humerus, or can in some embodiments be done in conjunction with the planning for the humerus, or humeral side of the joint. Such planning steps particular to the glenoid side of the joint can comprise analysis steps such as those depicted in FIGS. 1A-1I.

For example, a pre-operative planning method for the glenoid can comprise a step 101, as depicted in FIG. 1A, where the anterior edge 18 of glenoid implant 20 can be aligned 30 with anterior edge 16 of glenoid 12 of scapula bone 10 of a patient to be treated. In some embodiments, this step, as with other pre-operative analyses disclosed herein, can be accomplished virtually based on images, e.g. CT images or X-ray images, taken from a subject or patient prior to surgery. By aligning anterior edge 18 of glenoid implant 20 with anterior edge 16 of glenoid 12, data and information can be collected that informs the selection of a glenoid implant, and/or supports the creation of a patient-specific augmented glenoid implant, and/or supports the creation of a shoulder surgery guide device specific to the patient or subject to be treated.

Figure 1B:
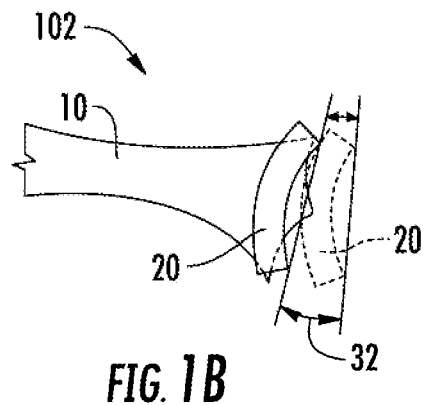
FIG. 1B is a schematic illustration of a step in a pre-operative planning method for designing a shoulder surgery guide where the retroversion of a glenoid implant is adjusted, according to an embodiment of the disclosed subject matter.

In some embodiments, a pre-operative planning method for the glenoid can comprise a step 102, as depicted in FIG. 1B, where the retroversion 32 of glenoid implant 20 is adjusted and/or measured. The retroversion is the placement or degree of posterior rotation of glenoid implant 20 when glenoid 12, including posterior wear 14 (see FIG. 1A), is reamed or otherwise resurfaced to accommodate glenoid implant 20. Such a measurement of retroversion 32 of glenoid implant 20 can be in comparison to the retroversion of the native glenoid in a subject to be treated. In some embodiments, adjusting the retroversion comprises adjusting the retroversion to be about 5 degrees (5°) to about 10 degrees (10°, with a maximum of 10°. In some embodiments, this analysis can be accomplished virtually based on images taken from a subject or patient prior to surgery. By measuring and/or adjusting the retroversion 32 of glenoid implant 20, data and information can be collected that informs the selection of a glenoid implant, and/or design and production of a patient-specific augmented glenoid implant, and/or supports the creation of a shoulder surgery guide device specific to the patient or subject to be treated.

Figure 1C:
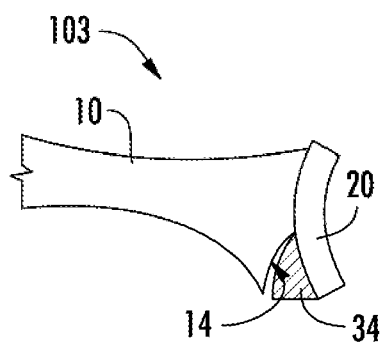
FIG. 1C is a schematic illustration of a step in a pre-operative planning method for designing a shoulder surgery guide where the augmentation of a glenoid implant is adjusted, according to an embodiment of the disclosed subject matter.

In some embodiments, a pre-operative planning method for the glenoid can comprise a step 103, as depicted in FIG. 1C, where a determination can be made as to the necessity of augmentation 34 to support glenoid implant 20. In some embodiments, particularly where glenoid 12 includes posterior wear 14 (or wear at other locations of glenoid 12 not depicted in FIG. 1C), augmentation can be necessary and/or desirable to provide adequate support for the placement and/or attachment of implant 20. Such a step or analysis can in some embodiments comprise adjusting, sizing and/or measuring augmentation 34 needed. In some embodiments, this analysis can be accomplished virtually based on images taken from a subject or patient prior to surgery. By assessing the need for augmentation 34, and/or determining the type and/or size of augmentation 34, data and information can be collected that informs the selection of a glenoid implant, and/or design and production of a patient-specific augmented glenoid implant, and/or supports the creation of a shoulder surgery guide device specific to the patient or subject to be treated.

Figure 1D:
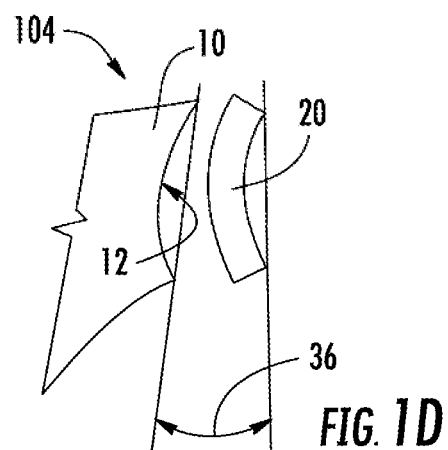
FIG. 1D is a schematic illustration of a step in a pre-operative planning method for designing a shoulder surgery guide where the inferior tilt of a glenoid implant is adjusted, according to an embodiment of the disclosed subject matter.

In some embodiments, a pre-operative planning method for the glenoid can comprise a step 104, as depicted in FIG. 1D, where the inferior tilt 36 of glenoid implant 20 can be measured and/or assessed. Such a measurement of inferior tilt 36 of glenoid implant 20 can be in comparison to the tilt of the native glenoid in a subject to be treated. In some embodiments, this analysis can be accomplished virtually based on images taken from a subject or patient prior to surgery. By assessing the inferior tilt 36 of glenoid implant 20, data and information can be collected that informs the selection of a glenoid implant, and/or supports the design and production of a patient-specific augmented glenoid implant, and/or supports the creation of a shoulder surgery guide device specific to the patient or subject to be treated.

Figure 1E:
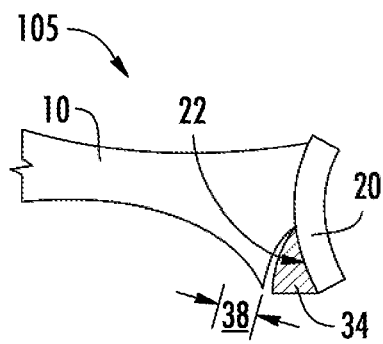
FIG. 1E is a schematic illustration of a step in a pre-operative planning method for designing a shoulder surgery guide where bone support for a glenoid implant is evaluated, according to an embodiment of the disclosed subject matter.

In some embodiments, a pre-operative planning method for the glenoid can comprise a step 105, as depicted in FIG. 1E, where the bone support 38 for glenoid implant 20 can be measured and/or assessed. Such an assessment can in some embodiments comprise characterizing and/or quantifying the amount or degree of bone support 38 for back side 22 of implant 20, taking into consideration posterior wear 14 (see, e.g., FIG. 1A or 1C; or wear at other locations of glenoid 12 not depicted). In some embodiments, this analysis can be accomplished virtually based on images taken from a subject or patient prior to surgery. By assessing the bone support 38, data and information can be collected that informs the selection of a glenoid implant, and/or supports the design and production of a patient-specific augmented glenoid implant, and/or supports the creation of a shoulder surgery guide device specific to the patient or subject to be treated.

Figure 1F:
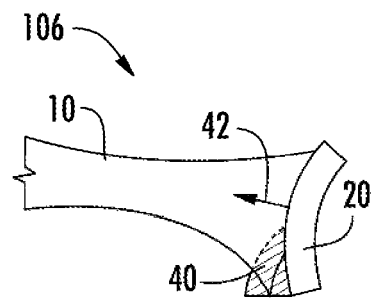
FIG. 1F is a schematic illustration of a step in a pre-operative planning method for designing a shoulder surgery guide where the medialization of a glenoid implant is adjusted by assessing the volumetric amount of bone needed to be removed by reaming, according to an embodiment of the disclosed subject matter.

In some embodiments, a pre-operative planning method for the glenoid can comprise a step 106, as depicted in FIG. 1F, where medialization 42 of glenoid implant 20 can be adjusted and/or characterized by assessing the volumetric amount 40 of bone needed to be removed by reaming. In some embodiments, this analysis can be accomplished virtually based on images taken from a subject or patient prior to surgery. By assessing the bone support 38, data and information can be collected that informs the selection of a glenoid implant, and/or supports the design and production of a patient-specific augmented glenoid implant, and/or supports the creation of a shoulder surgery guide device specific to the patient or subject to be treated.

Figure 1G:
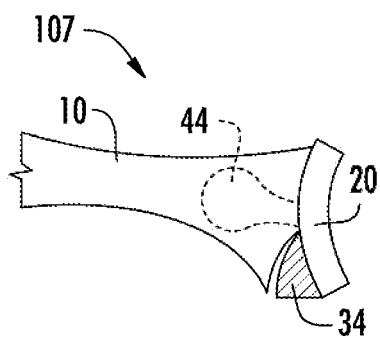
FIG. 1G is a schematic illustration of a step in a pre-operative planning method for designing a shoulder surgery guide where fixation support in the absence of central pegs that penetrate a vault medially is analyzed, according to an embodiment of the disclosed subject matter.

In some embodiments, a pre-operative planning method for the glenoid can comprise a step 107, as depicted in FIG. 1G, where fixation support in the absence of a central peg 44 that penetrates a vault medially of scapula 10 can be analyzed. In some embodiments, it is desirable to identify a location on the glenoid for attachment of a prosthesis using a peg or other fixation component without penetrating the anterior wall of the scapula. In some embodiments, this analysis can be accomplished virtually based on images taken from a subject or patient prior to surgery. By assessing the fixation support, data and information can be collected that informs the selection of a glenoid implant, and/or supports the design and production of a patient-specific augmented glenoid implant, and/or supports the creation of a shoulder surgery guide device specific to the patient or subject to be treated.

Figure 1H:
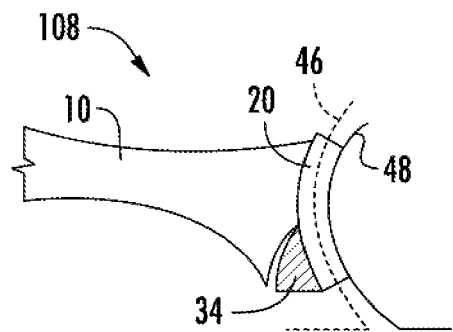
FIG. 1H is a schematic illustration of a step in a preoperative planning method for designing a shoulder surgery guide where a joint line is analyzed by comparing an original joint line and a new joint line, according to an embodiment of the disclosed subject matter.

In some embodiments, a pre-operative planning method for the glenoid can comprise a step 108, as depicted in FIG. 1H, where a joint line can be analyzed by comparing an original joint line 46 with a new joint line 48 as created when implant 20 is affixed to the glenoid surface of scapula 10. The degree to which the joint line changes or shifts, and/or the change in the angle, can be used in optimizing the implant 20 selection and/or placement. In some embodiments, analyzing the joint line, including comparing the original joint line and the new joint line, can comprise analyzing the humeral head lateralization. Humeral head lateralization can comprise the distance the humeral shaft is moved laterally relative to the scapula after the implants are placed. In some embodiments, this analysis can be accomplished virtually based on images taken from a subject or patient prior to surgery. By assessing the joint line, data and information can be collected that informs the selection of a glenoid implant, and/or supports the design and production of a patient-specific augmented glenoid implant, and/or supports the creation of a shoulder surgery guide device specific to the patient or subject to be treated.

Figure 1I:
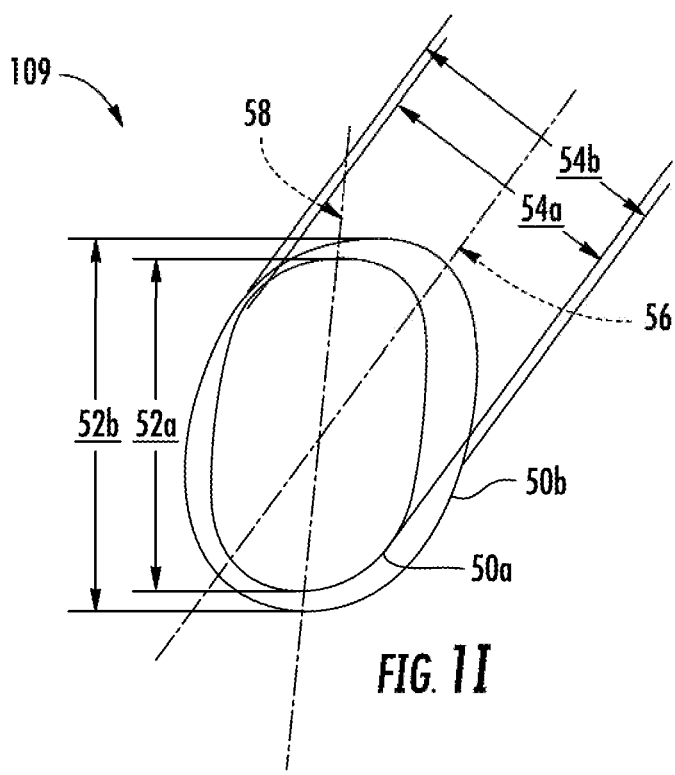
FIG. 1I is a schematic illustration of a step in a preoperative planning method for designing a shoulder surgery guide where widths of the glenoid implant and the glenoid bone are measured and matched after reaming and aligning inferior and superior axes of the glenoid implant and bone, according to an embodiment of the disclosed subject matter.

In some embodiments, a pre-operative planning method for the glenoid can comprise a step 109, as depicted in FIG. 1I, where the widths of the glenoid implant 50a and the glenoid bone 50b can be measured and matched after reaming and aligning inferior 56 and superior 58 axes of the glenoid implant and bone. Particularly, in some embodiments, a glenoid implant 50a height 52a and width 54a can be measured and aligned with a glenoid bone 50b height 52b and width 54b along inferior 56 and superior 58 axes. In some embodiments, this analysis can be accomplished virtually based on images taken from a subject or patient prior to surgery. By measuring the widths of the glenoid implant 50a and the glenoid bone 50b, and aligning inferior 56 and superior 58 axes of the glenoid implant and bone, data and information can be collected that informs the selection of a glenoid implant, and/or supports the design and production of a patient-specific augmented glenoid implant, and/or supports the creation of a shoulder surgery guide device specific to the patient or subject to be treated.

Such planning steps particular to the glenoid side of the joint can comprise analysis steps such as those depicted in FIGS. 1A-1I, and can comprise all or some of the steps depicted in FIGS. 1A-1I, and in some aspects can be done in any order desired. Alternatively, in some embodiments analysis steps particular to fixation elements can be performed first followed by analysis steps particular to joint articulation.

In some embodiments, a pre-operative planning method for designing and producing a shoulder surgery guide is provided for designing a guide for the humerus, or humeral bone. Such a method can be separate from a pre-operative planning method for the glenoid (discussed above and depicted in FIGS. 1a-1l), or can in some embodiments be done in conjunction with the planning for the glenoid, or glenoid side of the joint. Such planning steps particular to the humerus side of the joint can comprise analysis steps such as those depicted in FIGS. 2A-2D.

Figure 2A:
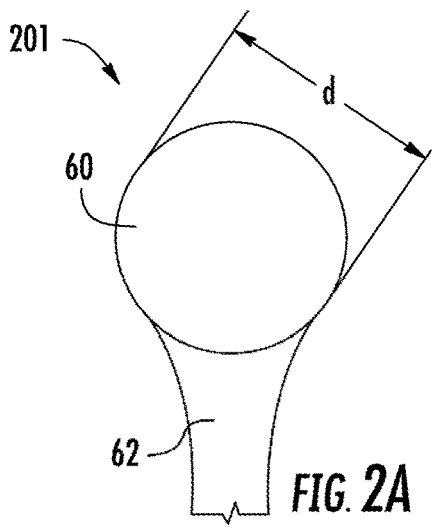
FIG. 2A is a schematic illustration of a step in a preoperative planning method for designing a shoulder surgery guide where the diameter of a humeral head is determined, according to an embodiment of the disclosed subject matter.

For example, a pre-operative planning method for the humerus can comprise a step 201, as depicted in FIG. 2A, where the diameter d of humeral head 60 of humerus 62 can be measured. In some embodiments, this analysis can be accomplished virtually based on images taken from a subject or patient prior to surgery. By measuring diameter d of humeral head 60, data and information can be collected that informs the selection of a humeral head implant, and/or supports the design and production of a patient-specific augmented glenoid implant, and/or supports the creation of a shoulder surgery guide device specific to the patient or subject to be treated.

Figure 2B:
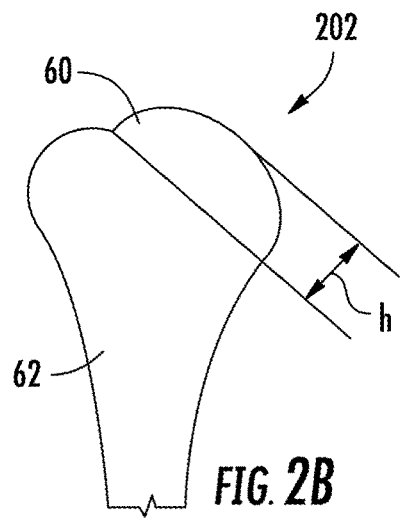
FIG. 2B is a schematic illustration of a step in a preoperative planning method for designing a shoulder surgery guide where the height of a humeral head is determined, according to an embodiment of the disclosed subject matter.

In some embodiments, a pre-operative planning method for the humerus can comprise a step 202, as depicted in FIG. 2B, where the height h of humeral head 60 of humerus 62 can be measured. In some embodiments, this analysis can be accomplished virtually based on images taken from a subject or patient prior to surgery. By measuring height h of humeral head 60, data and information can be collected that informs the selection of a humeral head implant, and/or supports the design and production of a patient-specific augmented glenoid implant, and/or supports the creation of a shoulder surgery guide device specific to the patient or subject to be treated.

Figure 2C:
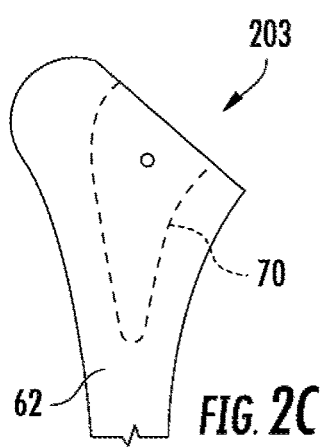
FIG. 2C is a schematic illustration of a step in a preoperative planning method for designing a shoulder surgery guide where the size of a humeral bone implant from Houndsfield units measured by computed tomography scan is determined, according to an embodiment of the disclosed subject matter.

In some embodiments, a pre-operative planning method for the humerus can comprise a step 203, as depicted in FIG. 2C, where the size of a humeral bone implant stem portion 70 can be determined from Houndsfield units (the Hounsfield scale, named after Sir Godfrey Newbold Hounsfield, is a quantitative scale for describing radiodensity) measured by CT scan. In some embodiments, this analysis can be accomplished virtually based on images taken from a subject or patient prior to surgery. By measuring the size of a humeral bone implant, data and information can be collected that informs the selection of a humeral head implant, and/or supports the design and production of a patient-specific augmented glenoid implant, and/or supports the creation of a shoulder surgery guide device specific to the patient or subject to be treated.

Figure 2D:
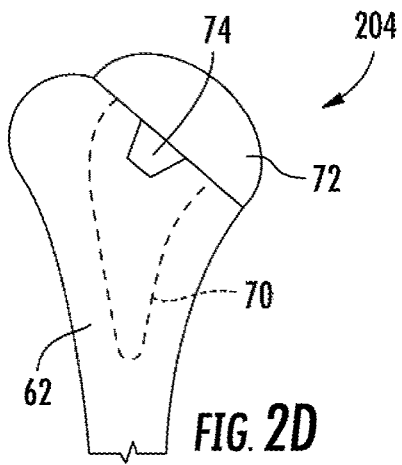
FIG. 2D is a schematic illustration of a step in a preoperative planning method for designing a shoulder surgery guide where a best fit size of implant from a range of sizes is determined, according to an embodiment of the disclosed subject matter.

In some embodiments, a pre-operative planning method for the humerus can comprise a step 204, as depicted in FIG. 2D, where a best fit size of humeral implant 72 (the humeral implant includes the humeral head 72 and the humeral stem 70) from a range of sizes can be determined. In some embodiments, the range of sizes can be selected from the group consisting of length of stem, size of humeral stem, diameter of stem, size diameter of head, height of head, and offset of the center spherical head compared to the center of the face of the humeral stem. In some embodiments, this analysis can be accomplished virtually based on images taken from a subject or patient prior to surgery. By determining the most appropriate size of humeral implant 72, data and information can be collected that informs the selection of a humeral head implant, and/or supports the design and production of a patient-specific augmented glenoid implant, and/or supports the creation of a shoulder surgery guide device specific to the patient or subject to be treated.

Such planning steps particular to the humeral side of the joint can comprise analysis steps such as those depicted in FIGS. 2A-2D, and can comprise all or some of the steps depicted in FIGS. 2A-2D, and in some aspects can be done in any order desired. Alternatively, in some embodiments analysis steps particular to joint articulation can be performed first followed by analysis steps particular to fixation elements.

Figure 3:
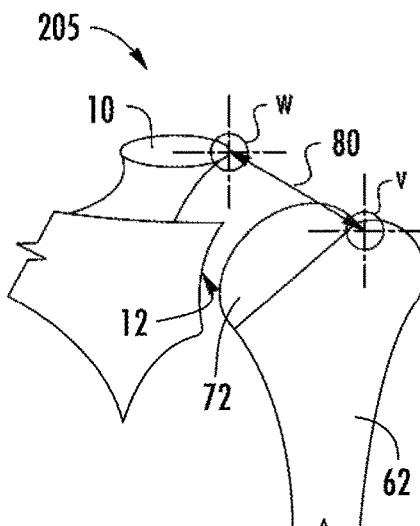
FIG. 3 is a schematic illustration of a step in a preoperative planning method for designing a shoulder surgery guide where vectors are compared in three dimensions to measure the distance of relocation of humeral tuberosity compared to the scapula, according to an embodiment of the disclosed subject matter.

In some embodiments, a pre-operative planning method for designing and/or producing an augmented glenoid implant and/or a shoulder surgery guide can comprise comparing vectors 80 in three dimensions to measure the distance of relocation of humeral tuberosity 72 compared to the scapula 10, as depicted in analysis 205 in FIG. 3. For example, there are 3 rotator cuff tendons that attach to the proximal humerus in the area of the greater tuberosity and the scapula. Such attachment points are depicted as v and w, respectively, in FIG. 3. These tendons control much of the rotation of the humerus about the scapula as well as having a part in elevating the humerus. If the vector resolved from these 3 tendons changes, kinematics and kinetics of the glenohumeral joint (joint comprising the glenoid and humerus) change. For example, changing the direction of vector 80 can change wear patterns and range of motion (ROM) of the implanted device versus the native joint. Additionally, in some embodiments, changing the magnitude of vector 80 by lengthening or increasing it with a joint prosthesis that is too large for the joint can result in decreased ROM, pain, and increased wear of the prosthetic components. Finally, changing the magnitude of vector 80 by decreasing or shortening it with a joint prosthesis that is too small for the joint can result in an unstable joint that may dislocate and can result in suboptimal mechanics for elevating the humerus. In some embodiments, this analysis can be accomplished virtually based on images taken from a subject or patient prior to surgery. By comparing vector 80 in three dimensions to measure the distance of relocation of humeral tuberosity 72 compared to the scapula 10, data and information can be collected that informs the selection of a humeral head implant, glenoid implant, and/or supports the design and production of a patient-specific augmented glenoid implant, and/or supports the creation of a shoulder surgery guide device specific to the patient or subject to be treated.

Figure 4:
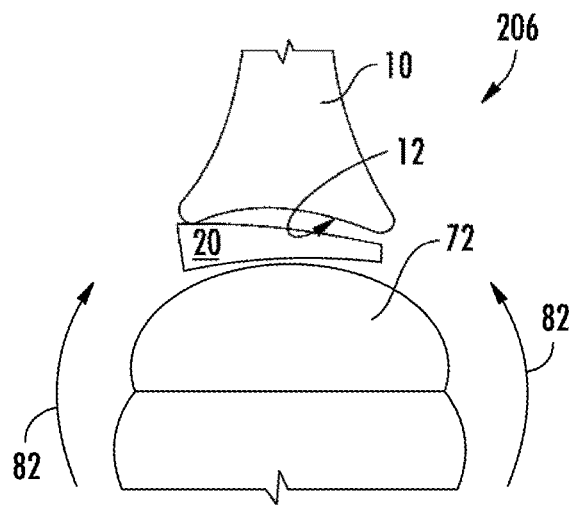
FIG. 4 is a schematic illustration of a step in a preoperative planning method for designing a shoulder surgery guide where range of motion analysis is conducted, including virtually positioning implants through extreme ranges of motion to measure impact locations and compensate for necessary functional range of motion, according to an embodiment of the disclosed subject matter.

In some embodiments, a pre-operative planning method for designing and/or producing an augmented glenoid implant and/or a shoulder surgery guide can comprise a step 206, as depicted in FIG. 4, where range of motion (ROM) analysis 82 can be conducted, including virtually positioning implants 20, 72 through extreme ranges of motion to measure impact locations and compensate for necessary functional ROM. In some embodiments, this analysis can be accomplished virtually based on images taken from a subject or patient prior to surgery. By measuring the ROM with respect to glenoid implants 20 and/or humeral implants 72, data and information can be collected that informs the selection of glenoid implant, a humeral head implant, and/or supports the design and production of a patient-specific augmented glenoid implant, and/or supports the creation of a shoulder surgery guide device specific to the patient or subject to be treated.

Figure 5:
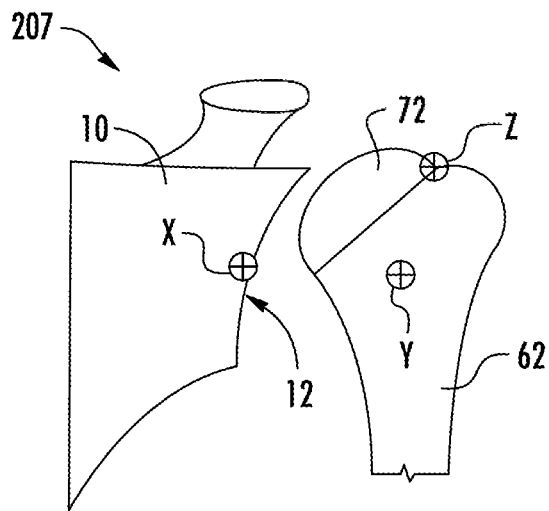
FIG. 5 is a schematic illustration of a step in a preoperative planning method for designing a shoulder surgery guide where soft tissue analysis comprising determining key soft tissue insertion points is conducted, according to an embodiment of the disclosed subject matter.

In some embodiments, a pre-operative planning method for designing and/or producing an augmented glenoid implant and/or a shoulder surgery guide can comprise a step 207, as depicted in FIG. 5, where soft tissue, e.g. muscle, analysis is conducted. In some aspects, soft tissue analysis can comprise determining and/or assessing soft tissue insertion points (e.g., X, Y and Z) and analyzing impacts on and/or impacts from use of one or more implants (glenoid and/or humeral). In some embodiments, four rotator cuff muscles and their attachments points can be analyzed. For example, in some aspects analysis can comprise the subscapularis that attaches at an attachment point Y near the lesser tuberosity and at an attachment point X near the anterior glenoid. In some aspects analysis can comprise the supraspinatus that attaches at an attachment point Z near the anterior greater tuberosity and above the scapular spine (shoulder blade; not shown). In some aspects, soft tissue analysis can comprise the infraspinatus that attaches at the greater tuberosity (posterior to supraspinatus) and below the scapular spine (posterior). In some aspects, soft tissue analysis can comprise the teres minor that attaches posterior on the humerus and on the inferior scapular boder. In some embodiments, this analysis can be accomplished virtually based on images taken from a subject or patient prior to surgery. By analyzing the soft tissue around the glenohumeral joint, data and information can be collected that informs the selection of a glenoid implant, a humeral head implant, and/or supports the design and production of a patient-specific augmented glenoid implant, and/or supports the creation of a shoulder surgery guide device specific to the patient or subject to be treated.

In some embodiments, the disclosed pre-operative planning methods can further comprise designing and/or producing an augmented glenoid implant and/or a shoulder surgery guide device, such as a glenoid placement guide, based upon parameters collected from the planning methods and analyses. In some embodiments, a designed augmented glenoid implant and/or shoulder surgery guide can be produced, wherein the produced surgery guide can be configured in accordance with parameters collected from the planning and analysis specific to the patient to be treated. In some aspects, a guide, and/or a glenoid prosthetic implant, can be produced or made using a three dimensional (3D) printing device. In some embodiments, a shoulder surgery guide device and/or glenoid implant produced as disclosed herein can comprise a polymeric or metallic material.

In some embodiments, the disclosed pre-operative planning methods can further comprise identifying a prosthetic shoulder implant, and/or designing a patient-specific augmented glenoid implant, and/or identifying a placement position for the prosthetic shoulder implant. The design and/or identification of a prosthetic shoulder implant and placement position takes into consideration at least one of the factors selected from the group consisting of adjustments in glenoid implant size, augmentation depth, augment position, positioning in six degrees of freedom, fixation type, fixation size, reaming depth, reaming diameter, reaming angle, and/or a combination thereof. The above method can further comprise a step of recommending implants and placement positions, with recommended adjustments in humerus stem size, length, head diameter, head height, head offset and rotation (axial). A prosthetic shoulder implant can in some embodiments comprise a glenoid implant.

In some embodiments, the above methods of designing and/or creating a glenoid implant, shoulder surgery guide, including a glenoid placement guide, based on pre-operative planning can further comprise one or more optimization steps. Such optimization steps can comprise the identification of procedural risks based on measurements of one or more of a plurality of factors. Such factors can in some embodiments comprise whether the glenoid face coverage is maximized (e.g. about 0 to about 2 mm), the overhang of the glenoid face is minimized (e.g. about 0 to about 3 mm), and/or the bone removal on the glenoid face is minimized, such as for example less than about 2 mm of depth. Continuing, in some embodiments such optimization factors can comprise whether the glenoid retroversion is less than about 5 degrees to about 10 degrees, the seating of the glenoid implant is greater than about 80%, i.e. about 80% of the back side of the glenoid implant is supported by or touching bone, whether there is minimized penetration of the glenoid cortical wall anteriorily (e.g. about 0 mm to about 3 mm), and/or the depth of any glenoid implant augment feature is as minimal as possible. Still yet, in some embodiments such optimization factors can comprise whether there is less than about 1 mm of difference between the anatomic joint line and the new joint line with implants, there is minimized penetration of the glenoid cortical wall anteriorily, and/or there is maximized bone thickness behind the glenoid, preferably greater than 3 mm. In some embodiments such optimization factors can comprise whether the orientation offset between the native glenoid and implant superior/inferior axis is minimized, preferably less than 5 degrees, the superior or inferior tilt versus native glenoid is minimized, preferably less than 5 degrees, there is less than about 5% to about 10% change in soft tissue length at extreme ranges of motion, there is maximized filing of the humeral metaphysis, in some embodiments greater than about 90% of metaphyseal bone filled based on and identification of metaphyseal bone by use of Houndsfield units, there is an absence of a humeral head overhang compared to the cut, or prepared surface of the humeral bone, there is minimal difference in humeral head diameter between anatomic and implant, in some embodiments less than about 3 mm, there is minimal difference in humeral head height between anatomic and implant, in some embodiments less than about 1 mm, and/or there is greater tuberosity to medial head edge comparison to anatomic, in some embodiments less than about 2 mm. In some embodiments, such procedural risks (any and/or all from the above list) can be determined virtually based on images taken from a subject prior to surgery.

Figure 6:
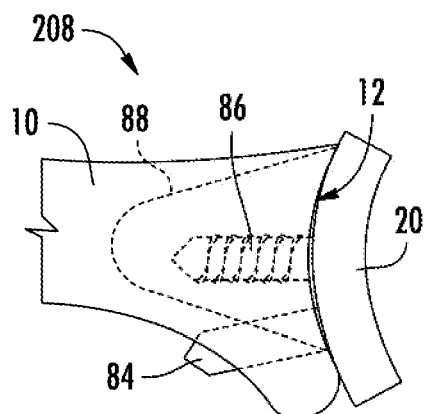
FIG. 6 is a schematic illustration of a step in a preoperative planning method for designing a shoulder surgery guide where penetration of the cortical wall anteriorily of the vault is assessed, according to an embodiment of the disclosed subject matter.

With respect to the above optimization steps that comprise the identification of procedural risks, in some embodiments the penetration of the cortical wall anteriorily of the vault can be assessed, as depicted in FIG. 6. FIG. 6 depicts step 208 of assessing the penetration of the cortical wall anteriorily of the vault 88 by a support structure 84 of glenoid implant 20. In some embodiments, an additional or alternate support structure 86 can be used to affix implant 20 to glenoid 12.

Figure 7:
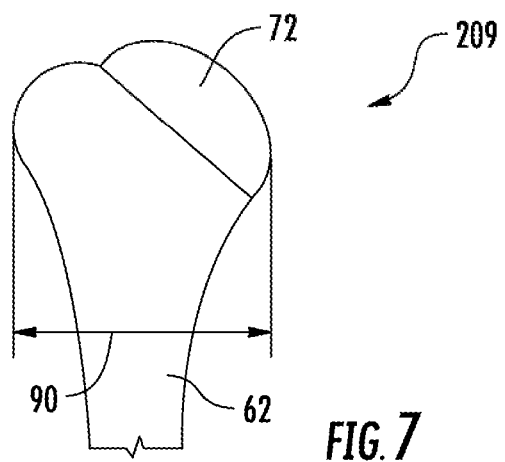
FIG. 7 is a schematic illustration of a step in a preoperative planning method for designing a shoulder surgery guide where the width of the greater tuberosity to medial head edge with an implant is compared to the anatomic width, according to an embodiment of the disclosed subject matter.

Also with respect to the above optimization steps that comprise the identification of procedural risks, in some embodiments the width of the greater tuberosity to medial head edge with an implant can be compared to the anatomic width. For example, in FIG. 7 the width 90 of the greater tuberosity to medial head edge with an implant 72 can be compared to the width of the anatomical humeral head.

In some aspects, the planning methods and analysis steps disclosed herein can be done pre-operatively. That is, they can be done prior to surgery in a virtual or software-based environment. Such virtual simulations can in some embodiments be based on images or scans taken from a subject prior to surgery. Currently available and future imaging techniques, e.g. computed tomography (CT), x-ray imaging, positron emission tomography (PET), ultrasound, etc., can be used to capture images and data to be used in simulation-based analysis and planning to identify suitable prosthetic implants and/or design surgery guides. In some embodiments, Digital Imaging and Communications in Medicine (DICOM), which is known as a standard for handling, storing, printing, and transmitting information in medical imaging, can be utilized. DICOM can in some embodiments provide for the integration of scanners, servers, workstations, printers, and network hardware from multiple manufacturers into a picture archiving and communication system (PACS). Application areas for DICOM Images are CT, MRI, PET, and Ultrasound, among others. By using images captured from a subject or patient to be treated, the analysis and results can be specific to the subject or patient and can take into consideration the particularities of that subject's condition.

In some aspects, when the pre-operative planning is conducted, particularly with respect to designing and producing an augmented glenoid implant and/or glenoid placement guide as disclosed herein, the actual morphologic form of the native glenoid bone of a patient to be treated is considered and imaged. In order for the fit and configuration of the glenoid implant to be correct, the form of the glenoid as found on a CT scan, for example, is used to create a "reverse image" that is incorporated in the implant design. Likewise, in order for the positioning of a glenoid placement guide to be correct, the form of the glenoid as found on a CT scan, for example, is used to create a "reverse image" that is incorporated in the guide design.

The subject matter described herein may be implemented in software in combination with hardware and/or firmware. For example, the subject matter described herein may be implemented in software executed by a processor. In one exemplary implementation, the subject matter described herein may be implemented using a computer readable medium having stored thereon computer executable instructions that when executed by the processor of a computer control the computer to perform steps. Exemplary computer readable media suitable for implementing the subject matter described herein include non-transitory devices, such as disk memory devices, chip memory devices, programmable logic devices, and application specific integrated circuits. In addition, a computer readable medium that implements the subject matter described herein may be located on a single device or computing platform or may be distributed across multiple devices or computing platforms.

As such, in some embodiments the disclosed pre-operative planning methods can further comprise providing a computer readable medium having stored thereon executable instructions that when executed by the processor of a computer control the computer to perform one or more of the planning method and/or analysis steps. For example, in some embodiments computer readable medium can have stored thereon executable instructions that when executed by the processor of a computer can control the computer to generate a virtual 3D model of an augmented or patient-specific glenoid implant and/or a glenoid guide device, e.g. a glenoid placement guide, reflecting one or more optimized parameters determined during pre-operative planning. Additionally, in some aspects, computer readable medium can have stored thereon executable instructions that when executed by the processor of a computer control the computer to control a 3D printing device in communication with the computer, whereby the 3D printing device can print a patient-specific, i.e. customized, augmented glenoid implant and/or a glenoid guide device or humeral guide device for use in shoulder replacement surgery in a patient for which pre-operative planning method steps were conducted.

Further, in some aspects of the disclosed methods, systems and devices, a computer readable medium can be provided having stored thereon executable instructions that when executed by a processor of a computer can control the computer to generate a virtual 3D model of a patient-specific, i.e. customized, augmented glenoid implant and/or a glenoid implant device or placement guide device reflecting one or more optimized parameters determined during pre-operative planning. Thus, in some embodiments a computer readable medium is provided, wherein the computer readable medium has stored thereon executable instructions that when executed by the processor of a computer control the computer to perform one or more of the planning method and/or analysis steps as disclosed herein.

It should be noted that the computers, computing devices, hardware and/or functionality described herein may constitute a special purpose test device. Further, computers, computing devices, hardware and/or functionality described herein can improve the technological field of pre-operative planning for shoulder surgery and can improve generation of virtual modeling systems.

The subject matter described herein for generating 3D models of glenoid and/or humeral implant devices, and/or for modeling and virtually simulating pre-operative shoulder surgery analysis improves the likelihood of a positive outcome from shoulder surgery. It should also be noted that a computing platform, computer, computing device, and/or hardware that implements the subject matter described herein may comprise a special purpose computing device usable to generate 3D models of glenoid and/or humeral implant devices, and/or for modeling and virtually simulating pre-operative shoulder surgery analysis.

As used herein, the term "node" refers to a physical computing platform including one or more processors and memory.

As used herein, the terms "function" or "module" refer to hardware, firmware, or software in combination with hardware and/or firmware for implementing features described herein.

In some embodiments a computer readable medium is provided, having stored thereon executable instructions that when executed by the processor of a computer control the computer to perform steps comprising generating a virtual three dimensional model of a glenoid and/or humeral guide reflecting one or more optimized parameters determined during pre-operative planning based on the above method steps. In some embodiments, a computer readable medium is provided, having stored thereon executable instructions that when executed by the processor of a computer control a 3D printing device in communication with the computer, whereby the 3D printing device prints a glenoid and/or humeral guide, or placement guide, for use in shoulder replacement surgery in a patient for which the optimization analysis was conducted.

Based on the pre-operative planning steps and analyses disclosed herein, in some embodiments glenoid implants, and particularly customized or patient-specific glenoid implant, including those with patient-specific augmentation, can be designed, simulated and in some instances produced for use in shoulder surgery. Such a surgery guide device is depicted in FIGS. 8A-16B and 12A-12I.

Figure 8B:
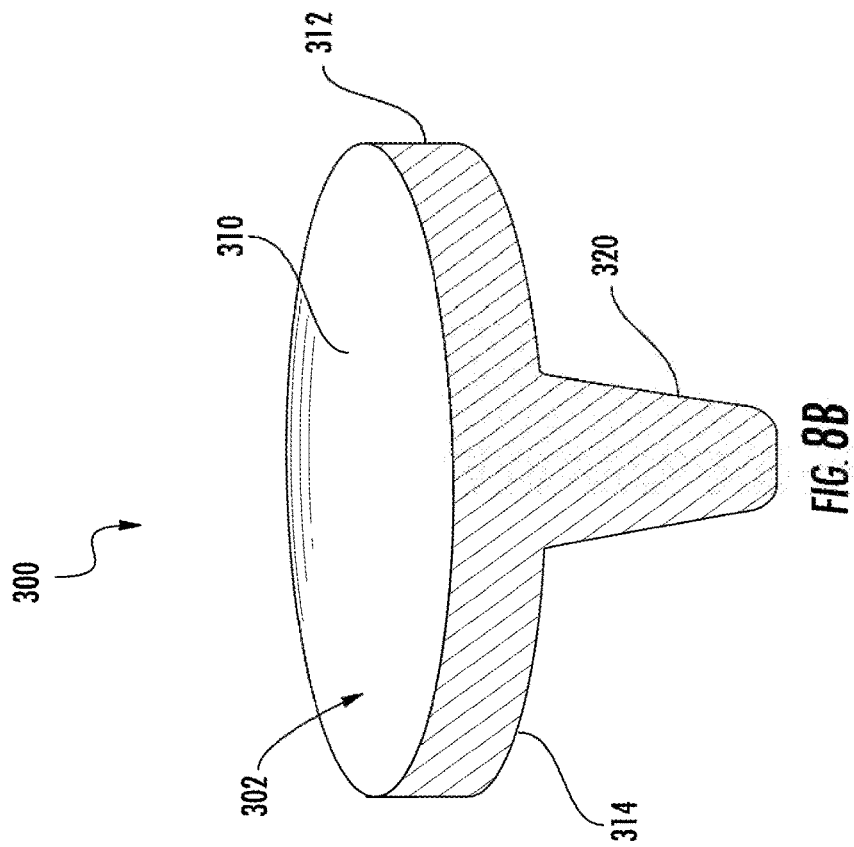
FIGS. 8A and 8B are perspective and cut-away views, respectively, of a glenoid implant.
Figure 8A:
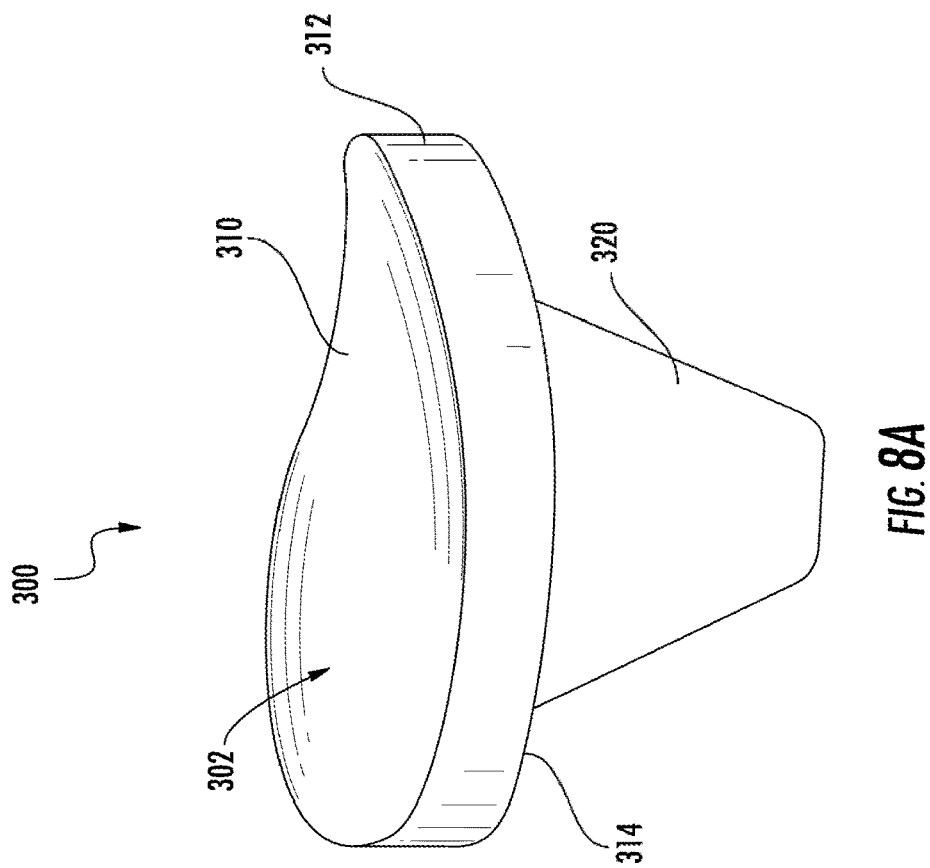

FIGS. 8A and 8B are perspective and cut-away views, respectively, of a standard glenoid implant 300. Such a glenoid implant can in some aspects comprise a central body 302, in some embodiments comprising a polyethylene material, wherein central body 302 can comprise a lateral articulating surface 310 on a first side (top side), sidewalls 312, a substantially flat second side (bottom side) 314, and one or more affixation components 320, such as for example a peg or keel (depicted in FIGS. 8A and 8B) extending from second or bottom side 314. As discussed herein, in some embodiments a glenoid implant 300 with a substantially flat bottom side 314 will not fit well against a glenoid of a patient, particularly where there is substantial wear. Thus, in some embodiments a glenoid implant with an augmented back or bottom side can provide a better fit or seat on the native glenoid surface of a patient.

Figure 9B:
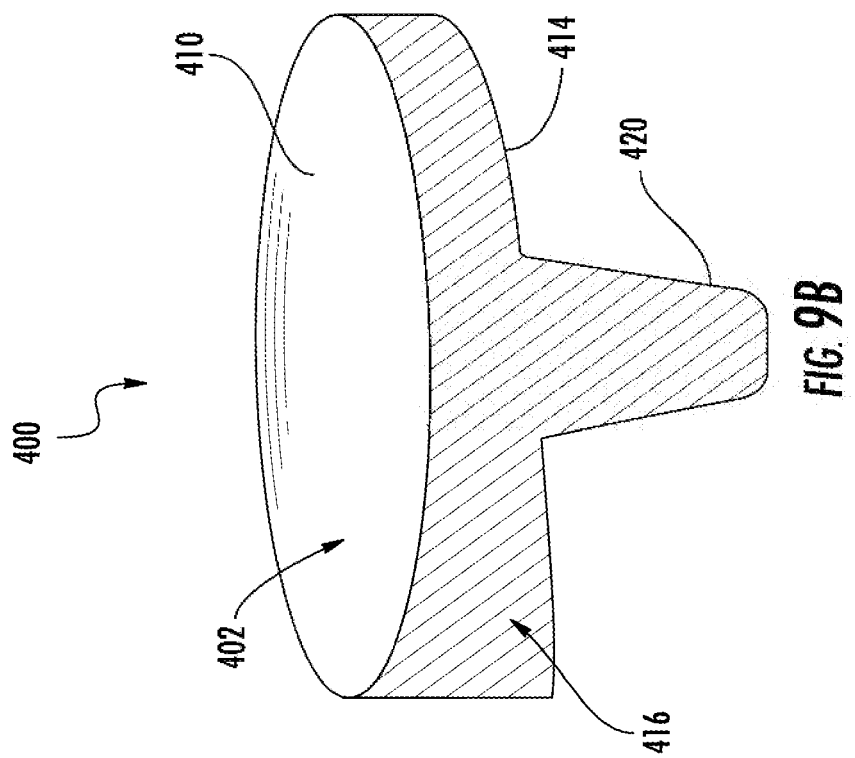
FIGS. 9A and 9B are perspective and cut-away views, respectively, of a glenoid implant.
Figure 9A:
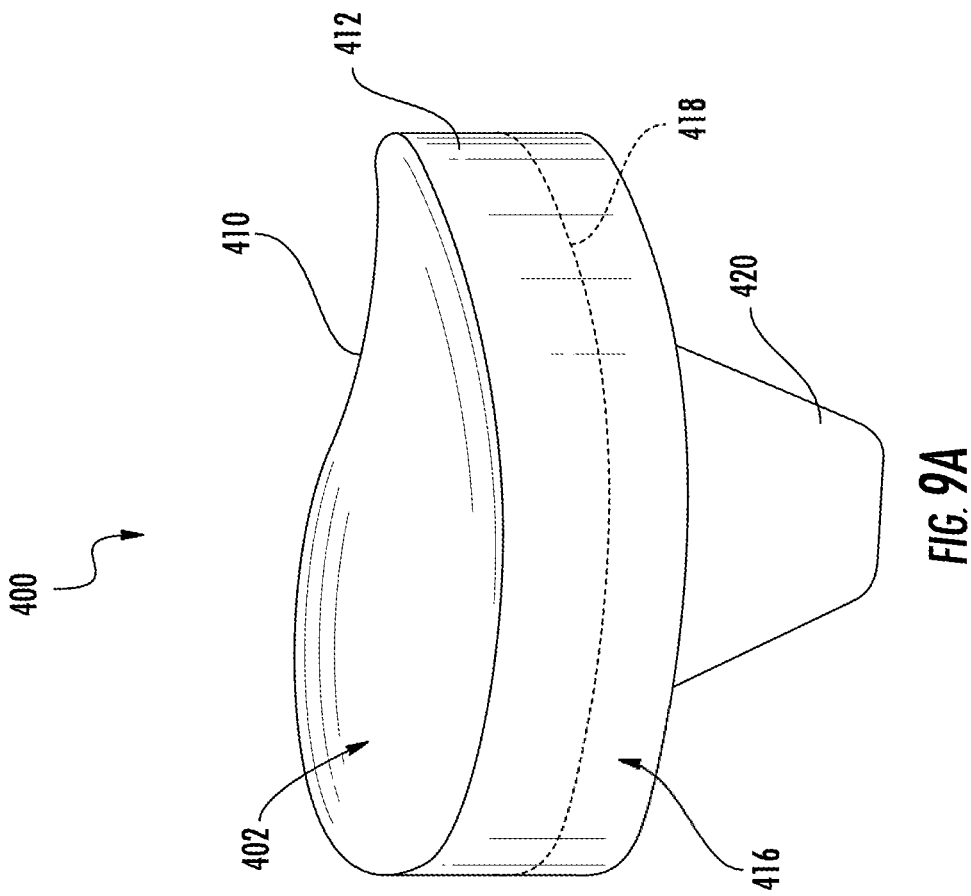

FIGS. 9A and 9B are perspective and cut-away views, respectively, of a glenoid implant 400 with an augmentation 416. Such a glenoid implant can in some aspects comprise a central body 402, in some embodiments comprising a polyethylene material, wherein central body 402 can comprise a lateral articulating surface 410 on a first side (top side), sidewalls 412, a substantially flat second side (bottom side) 414 (except where augmentation 416 exists), and one or more affixation components 320, such as for example a peg or keel (depicted in FIGS. 8A and 8B) extending from second or bottom side 314. Dashed line 418 depicts the location of bottom side) 414 in the absence of augmentation 416.

Figure 10B:
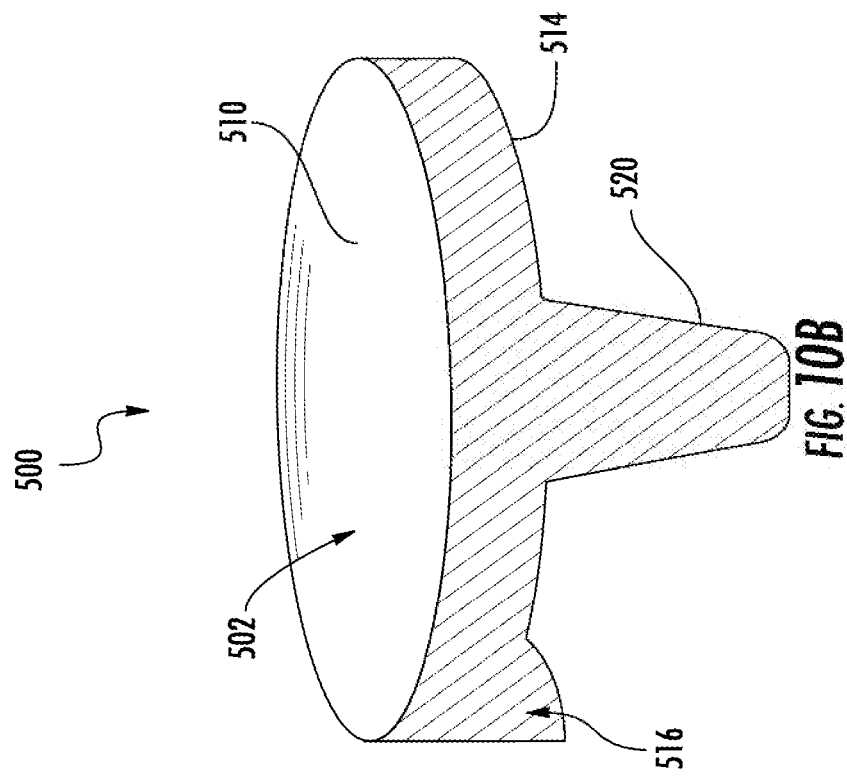
FIGS. 10A and 10B are perspective and cut-away views, respectively, of a glenoid implant with patient-specific backside augmentation.
Figure 10A:
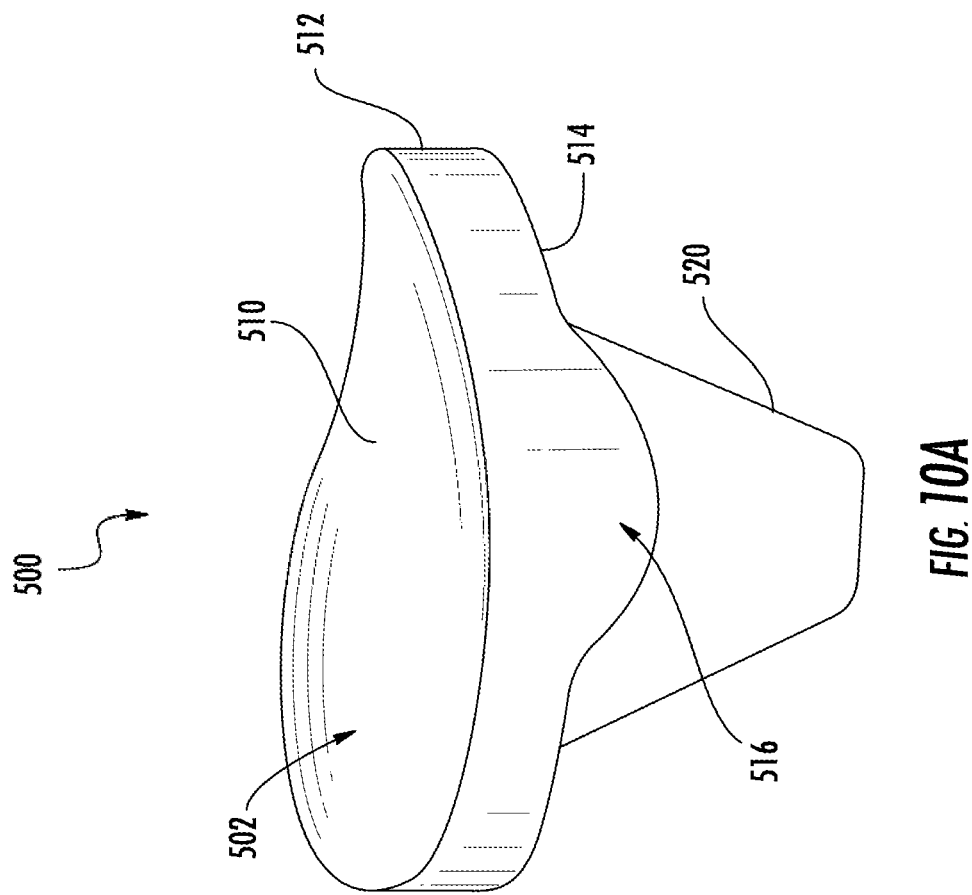

FIGS. 10A and 10B are perspective and cut-away views, respectively, of a glenoid implant 500 with patient-specific back-side augmentation 516. The patient-specific back-side augmentation 516 can be designed based on pre-operative planning and analysis as disclosed herein. Such a glenoid can be considered or referred to in some embodiments as a custom or adaptive glenoid implant that is tailored and/or designed specifically for a patient given the structure, shape and/or condition of the native glenoid surface of the patient. Such a glenoid implant can in some aspects comprise a central body 402, in some embodiments comprising a polyethylene material, wherein central body 402 can comprise a lateral articulating surface 410 on a first side (top side), sidewalls 412, a substantially flat second side (bottom side) 414 (except where augmentation 416 exists), and one or more affixation components 320, such as for example a peg or keel (depicted in FIGS. 8A and 8B) extending from second or bottom side 314.

In some embodiments, the central body, including the lateral articulating surface, can be substantially circular, oval or pear-shaped. In some embodiments, the shape of the glenoid implant approximates the shape of the natural glenoid cavity. In some aspects, the lateral articulating surface provides a surface upon which the humeral head can articulate.

In some embodiments, the augmentation of a glenoid disclosed herein can comprise an augmented feature or features extending from the second, or back side, of the glenoid implant. The second side of the glenoid implant is that which comes into contact with the bone of the scapula where the glenoid implant is seated, i.e. where the natural glenoid cavity was prior to insertion of the implant. Thus, the augmentation can in some embodiments enhance or improve the stability and contact between the glenoid implant and existing bone. In some aspects, an augmentation on the back side of a glenoid implant can be designed to align or match the shape and dimension of the cavity in the scapula where the glenoid is to be seated. By way of example and not limitation, in some aspects, the depth of the augmentation, size of the augmentation, and/or radial position of the augmentation on the second surface of the glenoid implant can be varied as desired given a particular situation, i.e. customized to fit the reamed glenoid cavity of the patient.

In some embodiments, a variable augmented glenoid implant or prosthesis is provided, wherein the variable augmentation is defined by one or more of the following: the depth of augmentation, the size of augmentation, the shape of the augmentation and/or the radial position of augmentation. By way of example and not limitation, the depth of the augmentation can range from about 2 mm to about 4 mm. Further, the augmentation can be small in size with respect to the size of the glenoid implant, e.g., can cover about 5%, 10%, 15%, 20%, 30%, 40%, 50%, or more of the back side of the glenoid implant, or can be large in size with respect to the size of the glenoid implant, e.g., can cover about 50%, 60%, 70%, 80%, 90%, 95% or greater of the back side of the glenoid implant. The shape of the augmentation can for example comprise a plate-like shape, sphere-like shape (fixed curvature, ellipsoid-like structure), cone like shape, a pyramid like shape or the like. The positioning of the augmentation on the second surface or back side of the glenoid can also vary, and can be located on the posterior and/or anterior side of the second surface, and/or at a superior and/or inferior location of the second surface of the glenoid implant. In some embodiments, the augmentation can be patient specific and/or patient tailored. In some aspects, the patient "specific" augmentation is generated by a geometric representation that best fits the joint surface, and does not consider that the joint surface necessarily needs to be altered in any way prior to implantation of the implant. In the case of a patient "tailored", the best fit implant is chosen, with a consideration for minimization of bone surface alteration to achieve minimally acceptable or optimal interface characteristics between the surface of the scapula bone and the implant. In some embodiments, the geometric representation can be plate (best fit plane), and/or spherical (best-fit-sphere), and/or ellipsoid (best-fit-ellipsoid). The radius of curvature could vary from $\infty$ to 10.

The geometric representation can depend on the wear surface and orientation. For example, a joint surface can be represented by 4 spheres with 4 different radi of curvature and 4 different sphere centers.

The augmentation can co-exist on the second surface of the glenoid implant along with a fixation component, e.g. a keel or peg. The fixation component can be located at any desirable position on the second surface of the glenoid implant, including for example in the center or medial position, at an inferior position, at a superior position, and/or in multiple locations, e.g. double fixation components.

In some aspects, the fixation component can have a free position on the backside surface and can be located according to the bony stock orientation of the patient in order to provide stable fixation and steady stress and strain distribution. The dimensions of the fixation elements can in some embodiments be patient tailored and their dimensions can be defined using correspondence matrix between a three dimensional (3D) bony structure of the patient and a statistical shape based atlas according to the following steps:

1. developing a registration between patient bone and statistical shape model of the bone of interest;
2. extract the principle modes representing the patient bone;
3. define the fixation configuration (position and dimensions) according to the corresponding modes; and
4. apply collision detection to confirm the configuration of the bone fixation.

Under the step of developing a registration between patient bone and statistical shape model of the bone of interest, a statistical mean shape model can be matched to the patient bone using rigid and/or non-rigid registration process in order to find the best fit between both shapes. During this process, the statistical mean shape can be deformed to fit well the size and the shape of the patient bone. Correspondence landmarks and/or regions, pathologic or not pathologic, can be used to guide the registration process.

Under the step of extracting the principle modes representing the patient bone, the shape parameters (Eigen values and eigen vectors) can be defined according to the deformation of the statistical mean shape. These shape parameters can be based on the principle variation modes of the model.

Under the step of defining the fixation configuration (position and dimensions) according to the corresponding modes, the extracted shape parameters can define the best fixation configuration based on the correspondence transformation between the mean SSM and the patient bone.

Finally, under the step of applying collision detection to confirm the configuration of the bone fixation, verifying the surrounding bone density can be done to evaluate the stability of the bone fixation.

In some aspects, and as discussed further herein (see, e.g. FIG. 17), a statistical shape model can be used as a component of any of the pre-operative analysis and modeling methods and techniques, including the use of a statistical appearance shape model, and/or parametric or non-parametric modeling.

By way of example and not limitation, a glenoid implant can be configured as described in Table 1, and as depicted in FIGS. 11A-16B. As would be appreciated by one of ordinary skill in the art, other configurations are possible without departing from the scope of the instant disclosure.

TABLE 1

|  | Example 1 (FIG. 11) | Example 2 (FIG. 12) | Example 3 (FIG. 13) | Example 4 (FIG. 14) | Example 5 (FIG. 15) | Example 6 (FIG. 16) |
| --- | --- | --- | --- | --- | --- | --- |
| Augmentation Depth | 2 mm | 2 mm | 4 mm | 4 mm | 2 mm | 2 mm |
| Augmentation Size | Small | Large | Large | Large | Small | Small |
| Augmentation Position | Posterior/ Superior | Posterior/ Superior | Posterior | Posterior/ Inferior | Posterior | Posterior/ Inferior |
| Augmentation shape | 2 Best-fit spheres | 2 Best fit spheres | 4 best-fit-spheres | 3 best fit spheres | 2 best-fit-sphere | 1 best-fit-sphere |
| Fixation Component Type/position | Centered | Inferior | Double | Superior | Double | Central |
| Fixation Component diameter/depth | 4 mm/8 mm | 5 mm/12 mm | 6 mm/9 mm | 6.5 mm/9.5 mm | 4 mm/8 mm | 4.5 mm/8.5 mm |

Figures 11A, 11B:
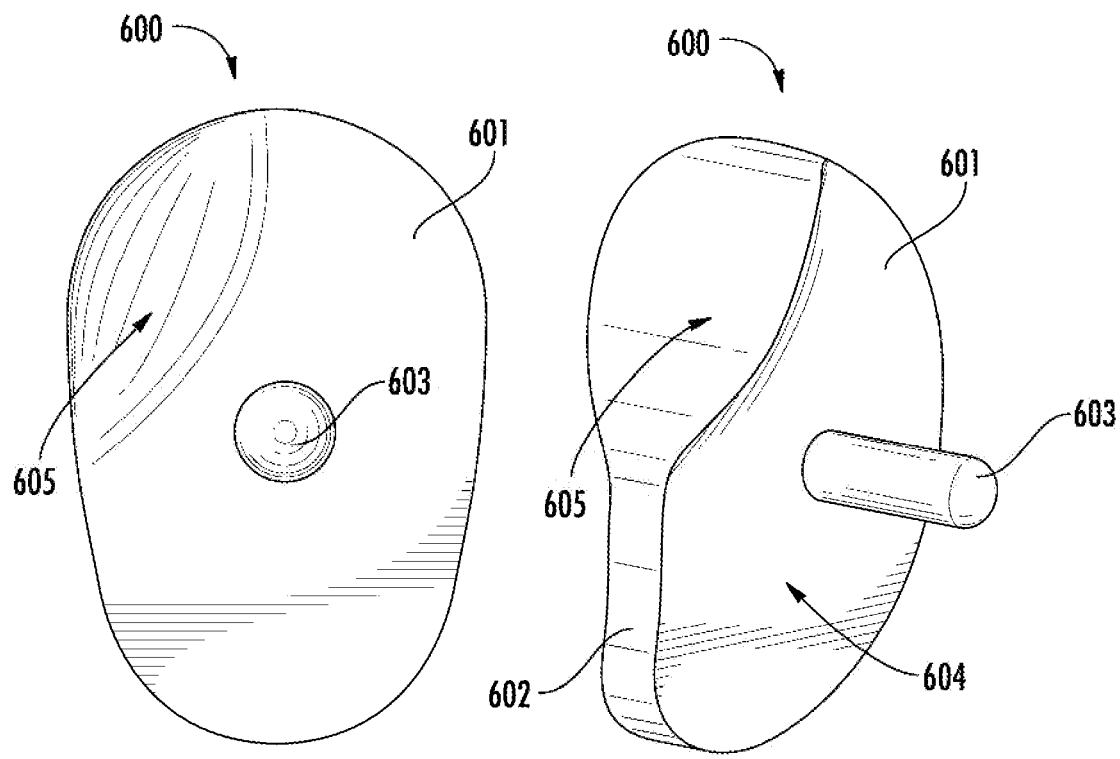
FIGS. 11A and 11B are rear and rear-perspective views, respectively, of an exemplary glenoid implant with patient-specific augmentation.

FIGS. 11A and 11B are rear and rear-perspective views, respectively, of an exemplary glenoid implant 600 with patient-specific augmentation 605. Such a glenoid implant can in some aspects comprise a central body 604, in some embodiments comprising a polyethylene material, wherein central body 604 can comprise a lateral articulating surface on a first side (front/top side), sidewalls 602, a substantially flat second side (bottom side) 601 (except where augmentation 605 exists), and an affixation component 603, such as for example a peg as depicted in in FIGS. 11A and 11B) extending from second or bottom side 601. The exemplary patient-specific augmentation 605 depicted in FIGS. 11A and 11B can comprise an about 2 mm deep, relatively small augmentation, located at a posterior/superior position with respect to the native glenoid surface to which it will be seated. The augmentation shape can comprise two best-fit spheres, and the affixation component can comprise a substantially centered single peg having a diameter of about 4 mm and a depth of about 8 mm.

Figures 12A, 12B:
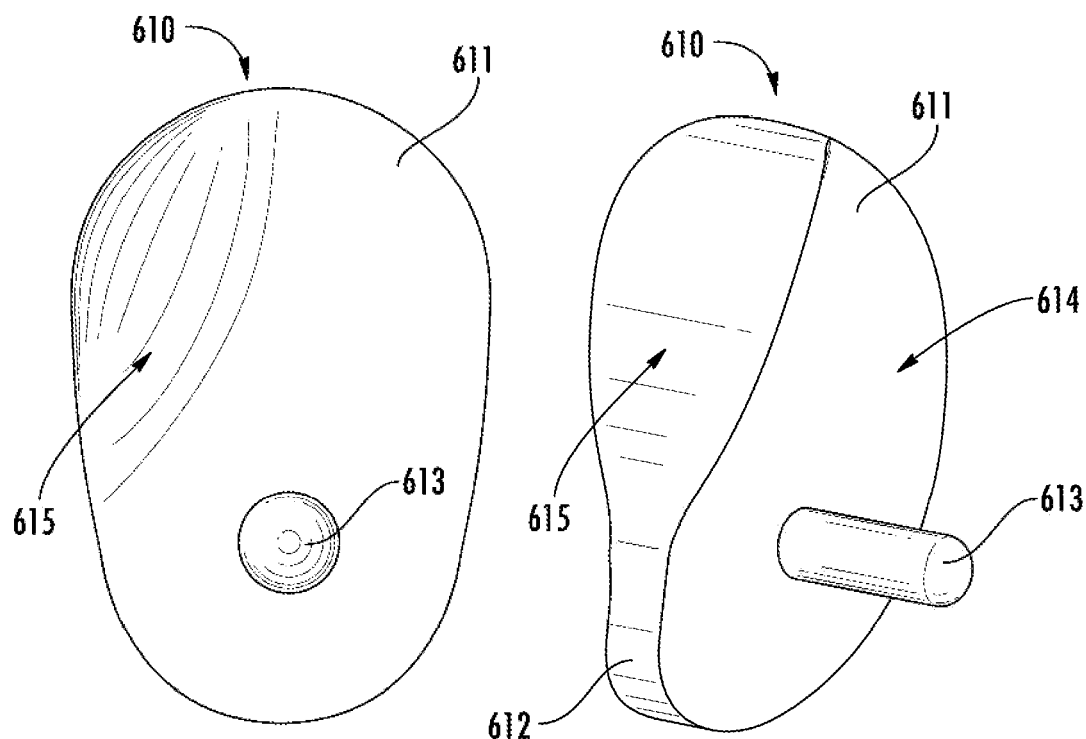
FIGS. 12A and 12B are rear and rear-perspective views, respectively, of an exemplary glenoid implant with patient-specific augmentation.

FIGS. 12A and 12B are rear and rear-perspective views, respectively, of an exemplary glenoid implant 610 with patient-specific augmentation 615. Such a glenoid implant can in some aspects comprise a central body 614, in some embodiments comprising a polyethylene material, wherein central body 614 can comprise a lateral articulating surface on a first side (front/top side), sidewalls 612, a substantially flat second side (bottom side) 611 (except where augmentation 615 exists), and an affixation component 613, such as for example a peg as depicted in in FIGS. 12A and 12B, extending from second or bottom side 611. The exemplary patient-specific augmentation 615 depicted in FIGS. 12A and 12B can comprise an about 2 mm deep, relatively large augmentation, located at a posterior/superior position with respect to the native glenoid surface to which it will be seated. The augmentation shape can comprise two best-fit spheres, and the affixation component can comprise a single peg located at an inferior position and having a diameter of about 5 mm and a depth of about 12 mm.

Figures 13A, 13B:
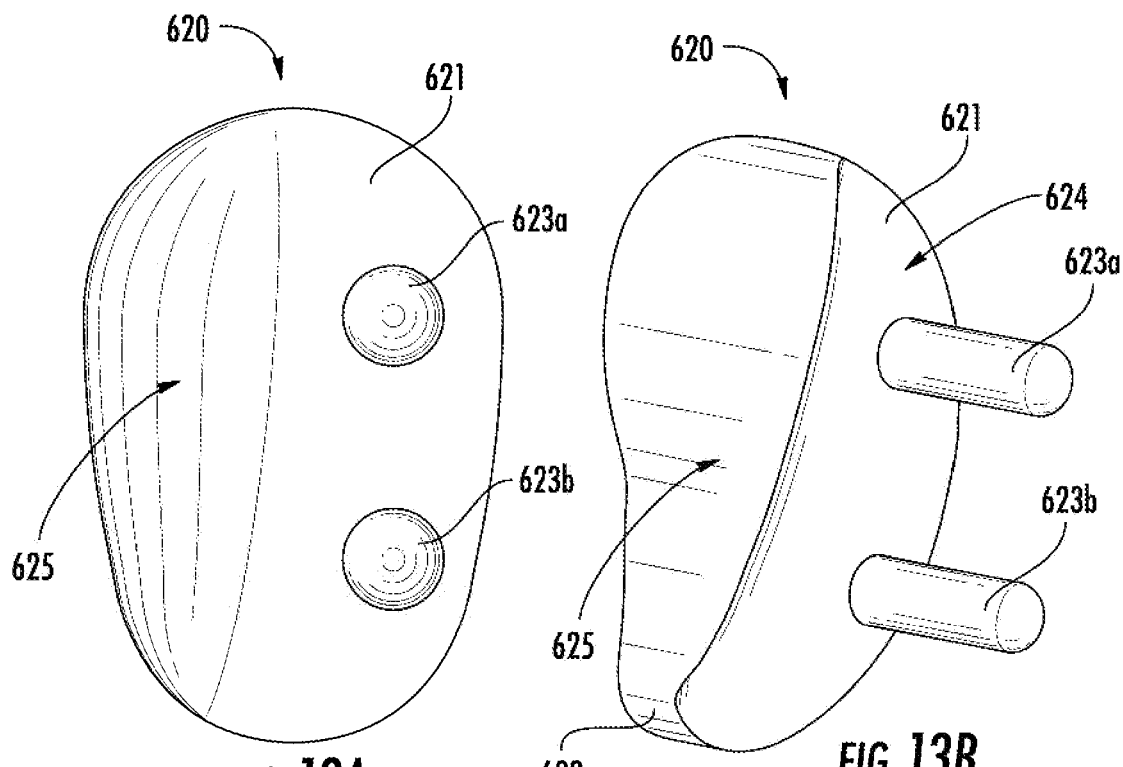
FIGS. 13A and 13B are rear and rear-perspective views, respectively, of an exemplary glenoid implant with patient-specific augmentation.

FIGS. 13A and 13B are rear and rear-perspective views, respectively, of an exemplary glenoid implant 620 with patient-specific augmentation 625. Such a glenoid implant can in some aspects comprise a central body 624, in some embodiments comprising a polyethylene material, wherein central body 624 can comprise a lateral articulating surface on a first side (front/top side), sidewalls 622, a substantially flat second side (bottom side) 621 (except where augmentation 625 exists), and an affixation component or components 623a/623b, such as for example pegs as depicted in in FIGS. 13A and 13B, extending from second or bottom side 621. The exemplary patient-specific augmentation 625 depicted in FIGS. 13A and 13B can comprise an about 4 mm deep, relatively large augmentation, located at a posterior position with respect to the native glenoid surface to which it will be seated. The augmentation shape can comprise four best-fit spheres, and the affixation components can comprise a pair of pegs having a diameter of about 6 mm and a depth of about 9 mm.

Figures 14A, 14B:
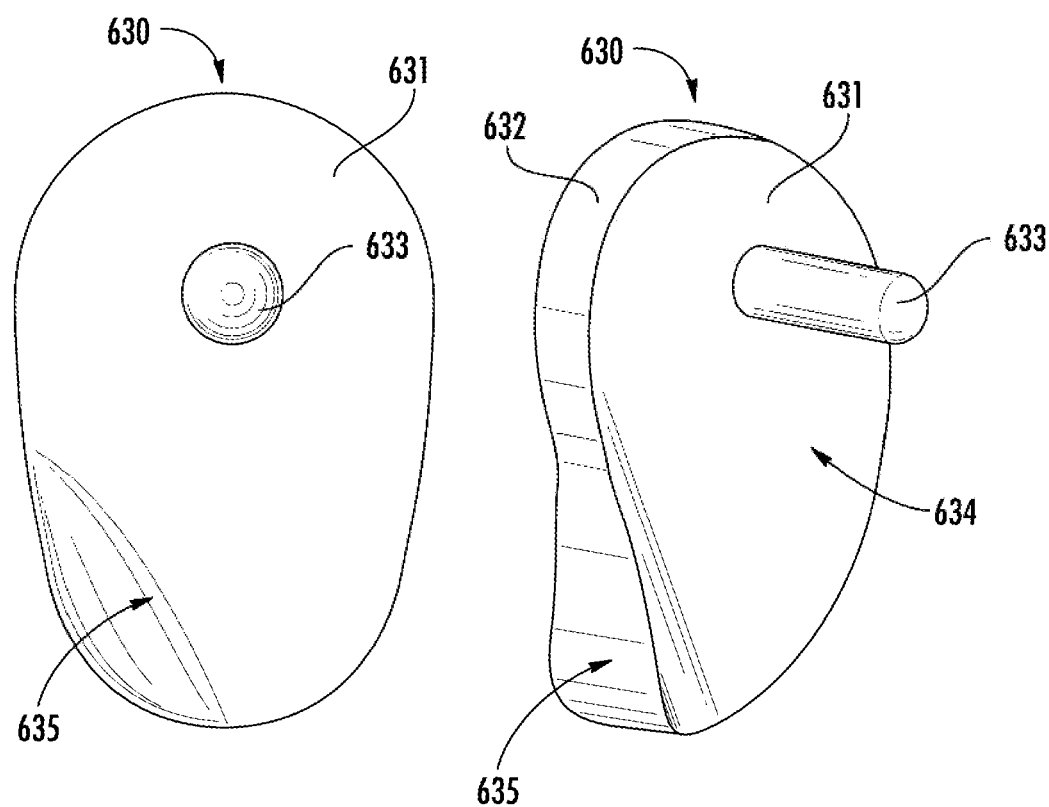
FIGS. 14A and 14B are rear and rear-perspective views, respectively, of an exemplary glenoid implant with patient-specific augmentation.

FIGS. 14A and 14B are rear and rear-perspective views, respectively, of an exemplary glenoid implant 630 with patient-specific augmentation 635. Such a glenoid implant can in some aspects comprise a central body 634, in some embodiments comprising a polyethylene material, wherein central body 634 can comprise a lateral articulating surface on a first side (front/top side), sidewalls 632, a substantially flat second side (bottom side) 631 (except where augmentation 635 exists), and an affixation component 633, such as for example a peg as depicted in in FIGS. 14A and 14B, extending from second or bottom side 631. The exemplary patient-specific augmentation 635 depicted in FIGS. 14A and 14B can comprise an about 4 mm deep, relatively large augmentation, located at a posterior/inferior position with respect to the native glenoid surface to which it will be seated. The augmentation shape can comprise three best-fit spheres, and the affixation component can comprise a single peg located at an superior position and having a diameter of about 6.5 mm and a depth of about 9.5 mm.

Figure 15A:
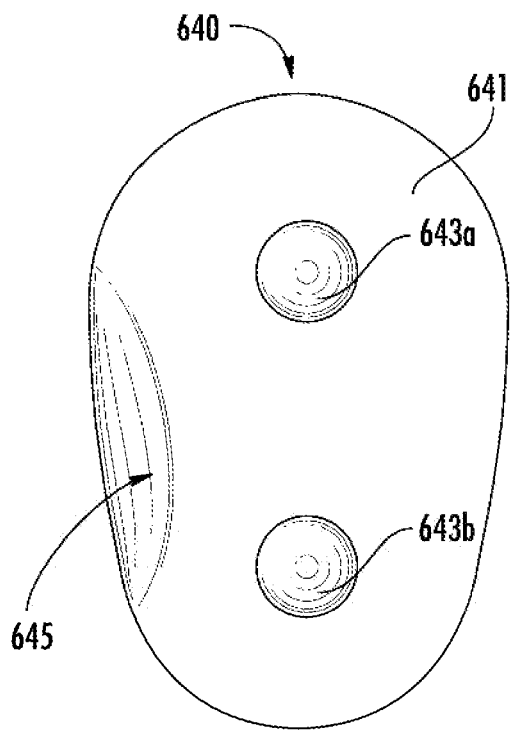
FIGS. 15A and 15B are rear and rear-perspective views, respectively, of an exemplary glenoid implant with patient-specific augmentation.
Figure 15B:
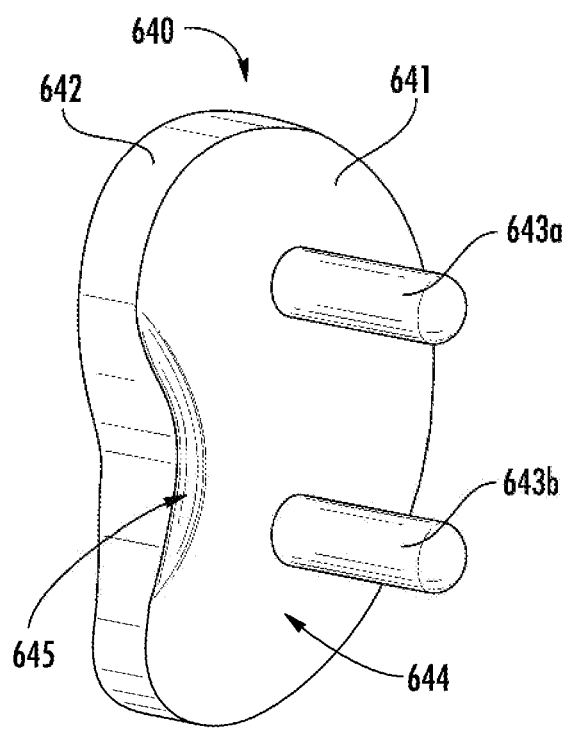

FIGS. 15A and 15B are rear and rear-perspective views, respectively, of an exemplary glenoid implant 640 with patient-specific augmentation 645. Such a glenoid implant can in some aspects comprise a central body 644, in some embodiments comprising a polyethylene material, wherein central body 644 can comprise a lateral articulating surface on a first side (front/top side), sidewalls 642, a substantially flat second side (bottom side) 641 (except where augmentation 645 exists), and an affixation component or components 643a/643b, such as for example pegs as depicted in in FIGS. 15A and 15B, extending from second or bottom side 641. The exemplary patient-specific augmentation 645 depicted in FIGS. 15A and 15B can comprise an about 2 mm deep, relatively small augmentation, located at a posterior position with respect to the native glenoid surface to which it will be seated. The augmentation shape can comprise two best-fit spheres, and the affixation components can comprise a pair of pegs having a diameter of about 4 mm and a depth of about 8 mm.

Figure 16A:
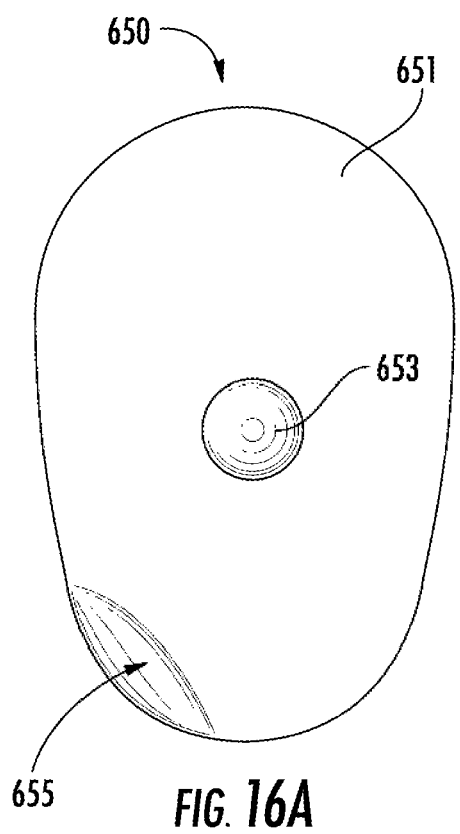
FIGS. 16A and 16B are rear and rear-perspective views, respectively, of an exemplary glenoid implant with patient-specific augmentation.
Figure 16B:
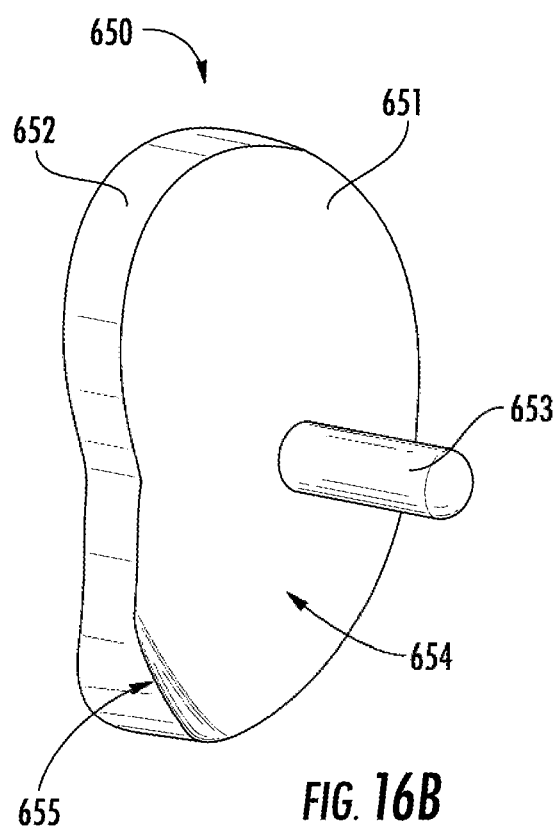

FIGS. 16A and 16B are rear and rear-perspective views, respectively, of an exemplary glenoid implant 650 with patient-specific augmentation 655. Such a glenoid implant can in some aspects comprise a central body 654, in some embodiments comprising a polyethylene material, wherein central body 654 can comprise a lateral articulating surface on a first side (front/top side), sidewalls 652, a substantially flat second side (bottom side) 651 (except where augmentation 655 exists), and an affixation component 653, such as for example a peg as depicted in in FIGS. 16A and 16B, extending from second or bottom side 651. The exemplary patient-specific augmentation 655 depicted in FIGS. 16A and 16B can comprise an about 2 mm deep, relatively small augmentation, located at a posterior/inferior position with respect to the native glenoid surface to which it will be seated. The augmentation shape can comprise one best-fit sphere, and the affixation component can comprise a single peg located at central position and having a diameter of about 4.5 mm and a depth of about 8.5 mm.

Figure 17:
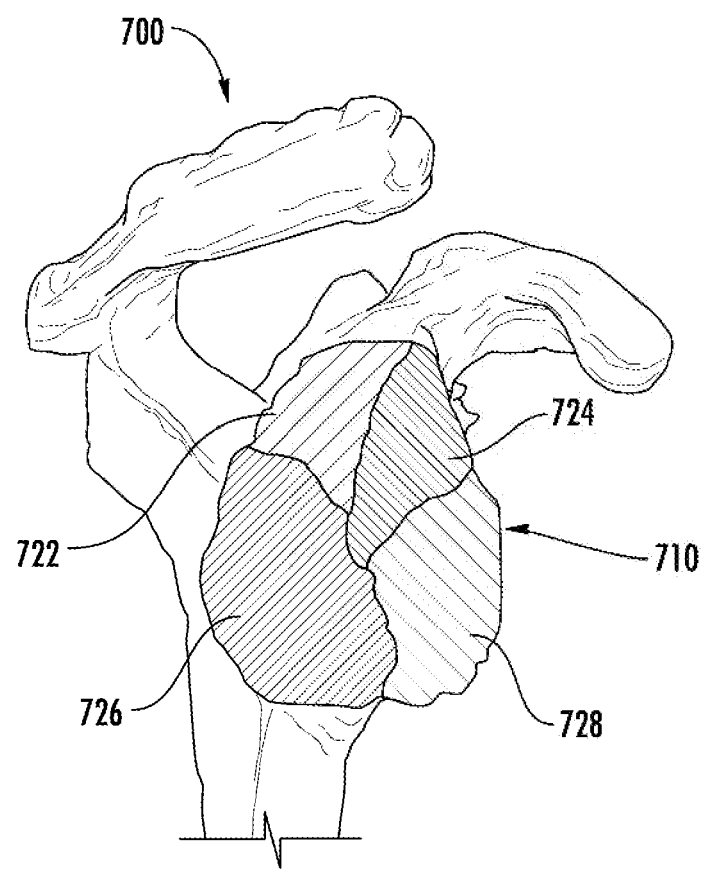
FIG. 17 is a schematic illustration of a scapula bone and glenoid surface depicted with defined zones based on statistical shape analysis.

As part of the pre-operative analysis, and design and production of a patient-specific glenoid implant, a statistical shape model can be used, including the use of a statistical appearance shape model, and/or parametric or non-parametric modeling. FIG. 17 is a schematic illustration of a scapula bone and glenoid surface depicted with defined zones based on statistical shape analysis. The multi-curvature glenoid backside can be analyzed according to statistical shape analysis. Based on the analysis of 70 pathologic scapula, principal statistical modes of the glenoid shape have been defined as depicted in FIG. 17. Based on these modes multiple backside zones with multiple curvatures can be defined. For example, a glenoid 710 on a scapula 700 as depicted in FIG. 17 can comprise a superior/posterior zone 722 that comprises about 13% of the glenoid surface, and having a radius of curvature (RoC) of about 22 mm. A superior/anterior zone 724 can comprise about 17% of the glenoid surface, and comprise a RoC of about 39 mm. An inferior/posterior zone 726 can comprise about 43% of the glenoid surface, and comprise a RoC of about 21 mm. An inferior/anterior zone 728 can comprise about 27% of the glenoid surface, and comprise a RoC of about 21 mm.

Figure 18A:
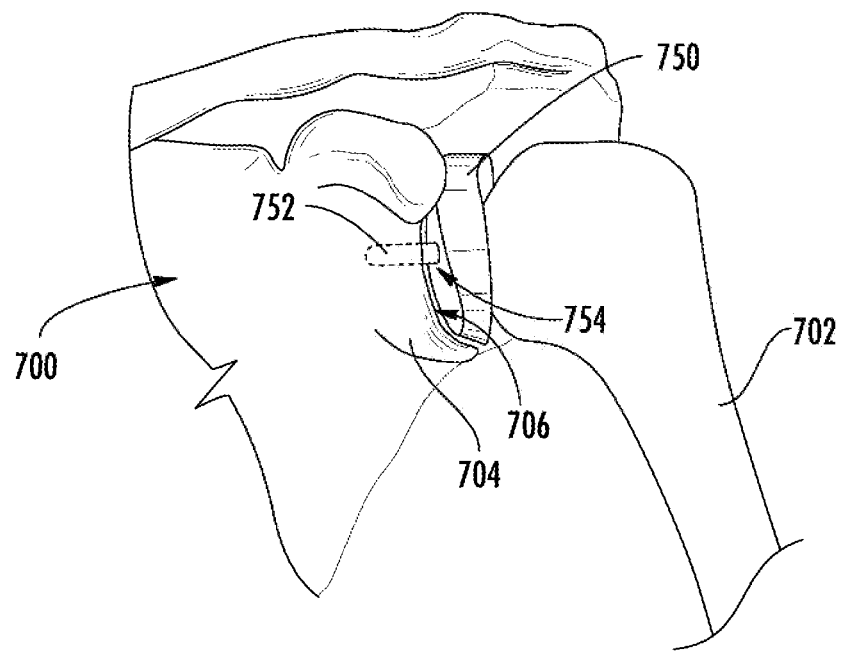
FIGS. 18A and 18B are anterior views of a scapula with a humerus bone, with the scapula having a glenoid implant secured thereto and the humerus head articulating thereon, where
Figure 18B:
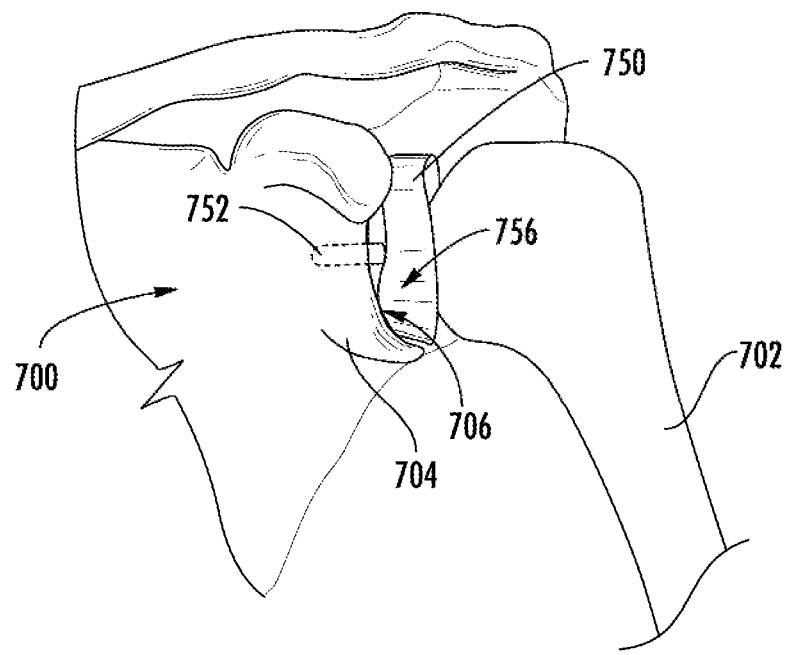

FIGS. 18A and 18B are anterior views of a scapula 700 with a humerus bone 702, with scapula 700 having a glenoid implant 750 secured thereto and the humerus head articulating thereon, where FIG. 18A depicts a glenoid implant 750 with no back-side augmentation and FIG. 18B depicting a glenoid implant 750 with back-side augmentation 756. In FIG. 18A glenoid implant 750 with no back-side augmentation is secured to glenoid 704 by, at least in part, augmentation 752, wherein a gap 754 exists between the back side of glenoid implant 750 and face 706 of glenoid bone 704. Alternatively, in FIG. 18B a glenoid implant 750 with back-side augmentation 756 is seated or affixed to glenoid 704, wherein augmentation 756 fills, or at least substantially fills, the gap such that the back-side of glenoid implant 750 more closely matches, and/or securely fits against, the face 706 of the native glenoid 704. Such augmentation can be configured to be patient-specific such that it matches the unique structure and/or surface character of a native glenoid of a patient to be treated.

Figure 19A:
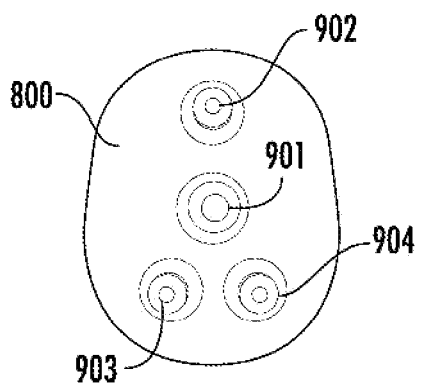
FIGS. 19A-19I are schematic illustrations of patient-specific glenoid implants with customized affixation components.
Figure 19B:
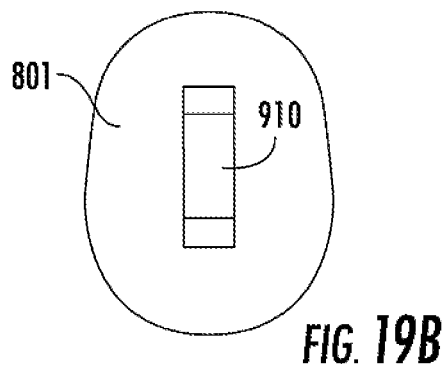
Figure 19C:
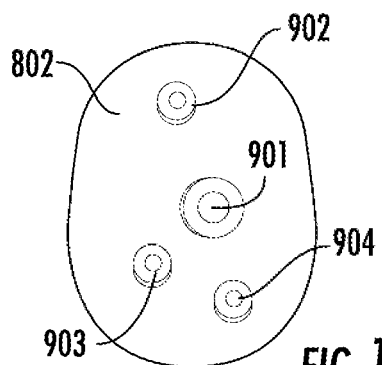
Figure 19D:
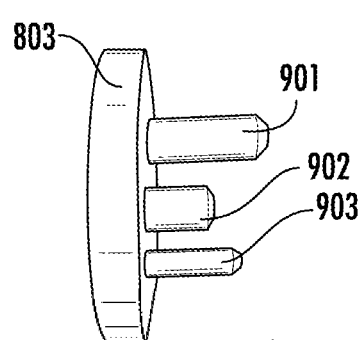
Figure 19E:
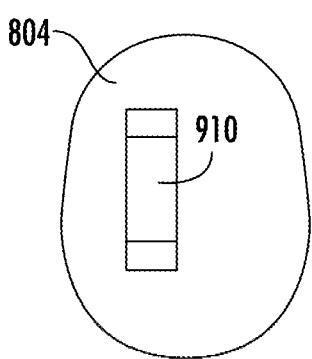
Figure 19F:
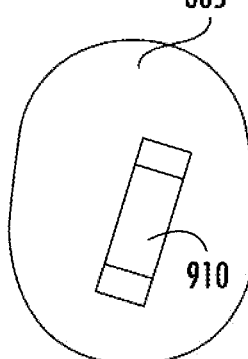
Figure 19G:
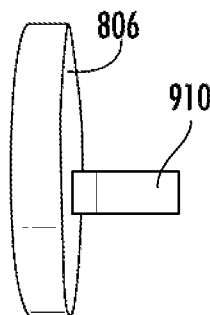
Figure 19H:
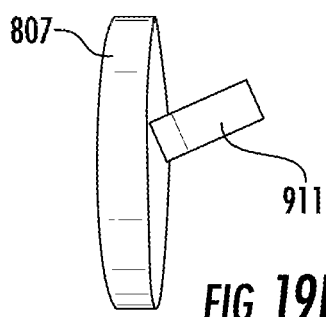
Figure 19I:
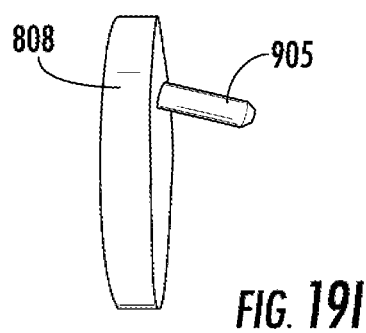

FIGS. 19A-19I are schematic illustrations of patient-specific glenoid implants with customized affixation components. In addition to, and/or in place of, customized or patient-specific augmentations on glenoid implants, in some embodiments affixation components can be customized to be patient-specific taking into consideration the native glenoid surface of the patient to be treated and based on pre-operative planning. FIG. 19A is a back-side view of a glenoid implant 800 with multiple pegs 901, 902, 903, 904 generally evenly distributed such that glenoid implant 800 is generally universally applicable to some patients. Likewise, glenoid implant 801 comprises a keel 910 centrally located and generally vertically oriented such that it is generally universally applicable to some patients. However, where the native glenoid surface of a patient to be treated requires a custom or adapted glenoid, and particularly affixation component(s), a patient-specific affixation configuration can be desirable. By way of example and not limitation, FIG. 19C depicts pegs 901, 902, 903, 904 spatially oriented in a manner that optimizes the securement of glenoid implant 802 to a given native glenoid bone. Moreover, the diameter of the pegs can be varied (see e.g. peg 901 versus peg 902) as needed to optimize securement of the implant. In addition to varying the orientation and diameter, the depth or length of pegs 901, 902, 903 can be varied as depicted in implant 803 in FIG. 19D. Where keels are used as affixation components, the orientation and/or positioning can be varied or adjusted as needed to optimize affixation to a native glenoid surface. For example, in glenoid 804 of FIG. 19E, keel 910 can be off-set from center. Also by way of example and not limitation, keel 910 can be angled, or tilted off vertical, in glenoid 805. Moreover, in some aspects, keel 910 can be located in a substantially inferior, as depicted in FIG. 19G, or superior position. Finally, keel 911 (FIG. 19H) or peg 905 (FIG. 19I) can be arranged such that they extend from the back-side of glenoid 807 and/or 808 in a substantially perpendicular position but angled at a desired degree to optimize the securement of the glenoid to a native glenoid surface. Combinations and/or variations of the exemplary embodiments depicted in FIGS. 19A-19I are within the scope of the instant disclosure.

In some embodiments, provided herein are pre-operative planning and shoulder surgery kits. Such kits can in some aspects comprise a set of instructions for performing pre-operative analysis steps as disclosed herein, and one or more guides, glenoid prosthetic devices and/or humeral prosthetic devices. In some embodiments, a kit can comprise a 3-D printing device for producing a guide and/or one or more glenoid and/or humeral prosthetic devices. In some embodiments, a kit can comprise a computer-readable medium for use in conducting the pre-operative planning, and designing a guide, glenoid implant and/or humeral implant based on input parameters gathered during the pre-operative planning. In some embodiments, the devices are customizable and/or modular in design such that the prosthetic device can be optimized for the patient based on the pre-operative planning analysis. In some aspects, a kit can comprise a range of glenoid implants having augmented back sides where the augmentation is selectable in terms of the augmentation size, shape, and position, both in the superior/inferior and posterior/anterior position. In some embodiments, a kit comprising a range of glenoid implants having augmented back is provided sides where the augmentation is selectable in terms of its size, shape, and position, where the position is defined by an angular and a radial position.

In some embodiments, methods of treating a patient, and/or surgical methods, are provided wherein one or more of the disclosed methods of analysis and optimization are performed on a patient in need of shoulder or other joint surgery. In some embodiments, methods of treating a patient are provided wherein a disclosed method of analysis and optimization is performed, an optimized guide is designed and created, and one or more glenoid and/or humeral implants are designed, created, and/or selected. In some embodiments, a method of treating a patient can comprise utilizing the pre-operative planning to design and optimize a guide and one or more glenoid and/or humeral implants, and the use of the guide to surgically implant the one or more glenoid and/or humeral prosthetic devices.

In some embodiments a patient can comprise a mammalian subject. In some embodiments, the patient can be a human subject, including an adult, adolescent or child.

While the following terms are believed to be well understood by one of ordinary skill in the art, the following definitions are set forth to facilitate explanation of the presently disclosed subject matter.

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Following long-standing patent law convention, the terms "a" and "an" mean "one or more" when used in this application, including the claims.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

The term "comprising", which is synonymous with "including," "containing," or "characterized by" is inclusive or open-ended and does not exclude additional, unrecited elements or method steps. "Comprising" is a term of art used in claim language which means that the named elements are present, but other elements can be added and still form a construct or method within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein, "significance" or "significant" relates to a statistical analysis of the probability that there is a non-random association between two or more entities. To determine whether or not a relationship is "significant" or has "significance", statistical manipulations of the data can be performed to calculate a probability, expressed as a "p value". Those p values that fall below a user-defined cutoff point are regarded as significant. In some embodiments, a p value less than or equal to 0.05, in some embodiments less than 0.01, in some embodiments less than 0.005, and in some embodiments less than 0.001, are regarded as significant. Accordingly, a p value greater than or equal to 0.05 is considered not significant.

As used herein, the terms "patient-specific", "customized" and/or "adaptive", when used in reference to a glenoid implant or humeral implant, can be used interchangeably and can in some embodiments refer to the specialization of such features taking into consideration factors specific to a patient to be treated, including for example characteristics acquired from pre-operative analysis and planning.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. An implant comprising a 3D printed body comprising:
a lateral articulating surface;
a medial surface; and
a sidewall extending around an edge of the lateral surface with an edge of the medial surface defining an outer perimeter,
wherein the medial surface includes an augmented portion sized and contoured to fit one patient, and wherein the medial surface comprises two radii of curvature corresponding to a native glenoid surface of the patient.

2. The implant of claim 1, wherein the augmented portion covers about 25% to 35% of the medial surface of the implant.

3. The implant of claim 1, wherein a radial location of the augmented portion is selected from the group consisting of a posterior location, an anterior location, a superior location, and an inferior location.

4. The implant of claim 1, wherein the implant comprises a fixation component extending from the medial surface.

5. The implant of claim 1, wherein the implant comprises at least one a polymeric, a metallic, a ceramic and a pyrolytic carbon material.

6. A method of planning a design of an implant comprising:
generating a virtual implant as a virtual three dimensional model of the implant comprising a plurality of adjustable parameters;

adjusting at least two of the plurality of adjustable parameters of the virtual implant by performing a virtual analysis comprising two or more of:
  aligning an anterior parameter of the virtual implant relative to an anterior edge of a bone image, wherein the bone image is based on a plurality of digital images corresponding to at least one of a bone or a group of cooperating bones of one patient;
  adjusting a retroversion parameter of the virtual implant;
  adjusting an augmentation parameter of the virtual implant;
  adjusting an inferior tilt parameter of the virtual implant;
  evaluating bone support parameters for the virtual implant;
  adjusting a medialization parameter of the virtual implant; or
  aligning inferior and superior axes of the virtual implant with respect to the bone image; and
designing an implant suitable for manufacturing by 3D printing based upon the plurality of adjustable parameters of the virtual implant resulting from the virtual analysis.

7. The method of claim 6, wherein the group of cooperating bones comprises a joint, the method further comprising analyzing a joint line, comprising comparing an original joint line and a new joint line, wherein the new joint line is substantially similar to the original joint line.

8. The method of claim 6, wherein the group of cooperating bones comprises a joint, the method further comprising comparing vectors in three dimensions which represent a distance and a direction between tendon and muscle insertions on a first bone of the group of bones and a second bone of the group of bones for measuring a distance of relocation of a portion of the first bone compared to the second bone.

9. The method of claim 8, further comprising determining a diameter of the portion of the first bone.

10. The method of claim 8, further comprising determining a height of the portion of the first bone.

11. The method of claim 8, further comprising determining a size of a first bone implant from the digital images.

12. The method of claim 11, further comprising determining a best fit size of the first bone implant from a range of sizes.

13. The method of claim 6, further comprising conducting a range of motion analysis, including virtually positioning the virtual implant through ranges of motion to measure impact locations and compensate for functional range of motion.

14. The method of claim 6, further comprising conducting a soft tissue analysis, comprising determining key soft tissue insertion points, measuring distances in three dimensions for comparison to pre-operative conditions, and assessing lengths corresponding to ranges of motion, such that total soft tissue length change or contraction is substantially maintained within anatomical ranges in order to substantially achieve common activities of daily living.

15. The method of claim 6, further comprising assessing and adjusting a thickness or a height of the virtual implant.

16. The method of claim 6, further comprising assessing and adjusting a depth of the bone image.

17. The method of claim 6, further comprising assessing and adjusting a thickness of at least one graft.

18. The method of claim 6, wherein the planning is pre-operative and virtually based on the plurality of digital images corresponding to the at least one of the bone or the group of cooperating bones of the patient.

19. The method of claim 18, further comprising adjusting dimensions of fixation elements of the virtual implant using a correspondence matrix between the bone image of the patient and a statistical shape based atlas, wherein adjusting the dimensions of the fixation elements of the virtual implant comprises:
  developing a registration between the bone image and a statistical shape model of the at least one of the bone or the group of cooperating bones;
  extracting principal modes of the bone image representing the at least one of the bone or the group of cooperating bones;
  defining a fixation configuration of the virtual implant with respect to the bone image according to the corresponding modes; and
  applying collision detection to confirm the fixation configuration of the virtual implant with respect to the bone image.

20. The method of claim 6, further comprising
identifying procedural risks by determining:
  whether coverage of a bone face is maximized;
  whether an overhang of the bone face is minimized;
  whether bone removal on the bone face is minimized;
  whether retroversion is less than about 5 to about 10 degrees;
  whether seating of the virtual implant is greater than about 80% of an implant coverage area;
  whether there is minimized penetration of a cortical wall anteriorly;
  whether there is greater than about 3 millimeter (mm) bone thickness behind a native glenoid surface of the bone;
  whether an orientation offset between the bone face and a superior axis or inferior axis of the virtual implant is less than about 5 degrees; and
  whether a superior or inferior tilt relative to the bone face is less than 5 degrees; and
wherein designing the implant comprises designing the implant based on the identified procedural risks comprising a 3D printed body comprising a lateral articulating surface, a medial surface, and a sidewall extending around an edge of the lateral surface and an edge of the medial surface defining an outer perimeter, wherein the medial surface includes an augmented portion sized to fit one patient, and wherein the medial surface comprises two radii of curvature corresponding to the native glenoid surface of the patient.

21. The method of claim 6, further comprising designing a shoulder surgery guide based upon the virtual analysis.

22. The method of claim 6, further comprising producing a shoulder surgery guide, wherein producing the shoulder surgery guide comprises using a 3D printing device.

23. The method of claim 6, further comprising recommending prosthetic shoulder implants and placement positions, selected from the group consisting of adjustments in glenoid implant size, augmentation depth, augment position, positioning in six degrees of freedom, fixation type, fixation size, reaming depth, reaming diameter, reaming angle(s) and/or a combination thereof.

24. Non-transitory computer readable storage media having stored thereon executable instructions that, when executed by one or more processors of a computer, control the computer to perform the planning method of claim 6.

25. The non-transitory computer readable storage media of claim 24, wherein the instructions control the computer to generate the virtual three dimensional model of the implant reflecting the plurality of adjustable parameters of the virtual implant as adjusted during the planning method.

26. The non-transitory computer readable storage media of claim 24, wherein the instructions control the computer to control a 3D printing device in communication with the computer, whereby the 3D printing device prints the implant for use in joint replacement surgery in the patient.

27. The non-transitory computer readable storage media of claim 24, wherein the instructions control the computer to generate the virtual three dimensional model of the implant reflecting adjustments to the at least two of the plurality of adjustable parameters of the virtual implant.

28. A method of treating a patient comprising:
completing the planning method of claim 6; and
manufacturing the implant based on the planning.

29. The method of claim 28, wherein the patient comprises a patient in need of shoulder replacement surgery.

30. The method of claim 28, wherein the implant comprises an augmented glenoid implant, wherein the augmentation is specific to the patient.

31. A method of planning a design of an implant comprising:
generating a virtual three dimensional model of the implant comprising at least two adjustable parameters;
adjusting the at least two adjustable parameters of the virtual three dimensional model by performing a virtual analysis comprising:
aligning at least a first parameter of the virtual three dimensional model of the implant relative to an edge of a bone image, wherein the bone image is based on a plurality of digital images corresponding to at least one of a bone or a group of cooperating bones of one patient;
evaluating bone support parameters for the virtual three dimensional model of the implant;
adjusting at least a second parameter of the virtual three dimensional model of the implant to adjust the bone support parameters for the three dimensional model of the implant with respect to the bone image;
measuring and matching widths of the virtual three dimensional model of the implant and the bone image after virtually reaming and virtually aligning axes of the virtual three dimensional model of the implant and the bone image; and
manufacturing the implant by 3D printing based upon the virtual three dimensional model of the implant after adjustment of the at least two adjustable parameters of the virtual three dimensional model of the implant.

* * * * *